(12) United States Patent
Marzu et al.

(10) Patent No.: US 12,055,522 B2
(45) Date of Patent: Aug. 6, 2024

(54) RAPID STALK STRENGTH ASSESSMENT

(71) Applicant: Monsanto Technology LLC, St. Louis, MO (US)

(72) Inventors: Jen Marzu, St. Louis, MO (US); Jonathan N. Nordby, St. Louis, MO (US); Jerald K. Pataky, St. Louis, MO (US); Boyan N. Peshlov, St. Louis, MO (US); Roger A. Weyhrich, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 939 days.

(21) Appl. No.: 17/054,579

(22) PCT Filed: May 30, 2019

(86) PCT No.: PCT/US2019/034602
§ 371 (c)(1),
(2) Date: Nov. 11, 2020

(87) PCT Pub. No.: WO2019/232179
PCT Pub. Date: Dec. 5, 2019

(65) Prior Publication Data
US 2021/0181078 A1   Jun. 17, 2021

Related U.S. Application Data

(60) Provisional application No. 62/679,179, filed on Jun. 1, 2018.

(51) Int. Cl.
*G01N 3/06* (2006.01)
*G01N 33/00* (2006.01)
(Continued)

(52) U.S. Cl.
CPC ......... *G01N 3/068* (2013.01); *G01N 33/0098* (2013.01); *G06T 7/0012* (2013.01);
(Continued)

(58) Field of Classification Search
CPC ............... G01N 3/068; G01N 33/0098; G01N 2203/0053; G06T 7/0012;
(Continued)

(56) References Cited

U.S. PATENT DOCUMENTS

| 618,805 A | * | 1/1899 | Pridmore | ............... A01D 45/02 |
| | | | | 56/69 |
| 5,044,210 A | * | 9/1991 | Kuhn | ..................... A01D 75/00 |
| | | | | 73/865.3 |

(Continued)

FOREIGN PATENT DOCUMENTS

| CN | 106888679 A | * | 6/2017 | ............. A01D 45/02 |
| CN | 115272187 A | * | 11/2022 | ............... G06T 5/30 |

(Continued)

OTHER PUBLICATIONS

International Search Report for PCT/US2019/034602 mailed Aug. 27, 2019.
Written Opinion for PCT/US2019/034602 mailed Aug. 27, 2019.

*Primary Examiner* — Arpad Fabian-Kovacs
(74) *Attorney, Agent, or Firm* — Sandberg Phoenix & von Gontard, P.C.

(57) ABSTRACT

A system for post-harvest or at-harvest determination of pre-harvest strength of a corn stalk wherein the system comprises a stalk stump cutter structured and operable to cut a discarded post-harvest stalk stump to provide a substantially flat and even cross-sectional surface of the stalk stump, an imaging device structured and operable to acquire image data of the stalk stump cross-section, and a computer based data processing system structured and operable to analyze (Continued)

the image data and determine a pre-harvest stalk strength of the corresponding stalk.

19 Claims, 13 Drawing Sheets

(51) Int. Cl.
 G06T 7/00 (2017.01)
 A01D 34/68 (2006.01)
 A01D 34/73 (2006.01)
 A01D 45/02 (2006.01)
 G01S 19/13 (2010.01)

(52) U.S. Cl.
 CPC .............. A01D 34/68 (2013.01); A01D 34/73 (2013.01); A01D 45/028 (2013.01); G01N 2203/0053 (2013.01); G01S 19/13 (2013.01); G06T 2207/30188 (2013.01); G06T 2207/30252 (2013.01)

(58) Field of Classification Search
 CPC .......... G06T 2207/30188; G06T 2207/30252; A01D 34/68; A01D 34/73; A01D 45/028; A01D 45/02; A01D 34/8355; A01D 41/127; G01S 19/13; A01B 79/003
 See application file for complete search history.

(56) References Cited

U.S. PATENT DOCUMENTS

| 5,173,079 | A | | 12/1992 | Gerrish | |
|---|---|---|---|---|---|
| 5,953,895 | A | * | 9/1999 | Hobbs | A01D 34/8355 56/10.2 G |
| 6,185,990 | B1 | * | 2/2001 | Missotten | A01B 79/005 56/10.2 A |
| 9,320,196 | B2 | * | 4/2016 | Dybro | G01N 33/0098 |
| 10,178,828 | B2 | * | 1/2019 | Hendrickson | G01N 33/0098 |
| 11,758,848 | B2 | * | 9/2023 | Eichhorn | G01B 21/06 73/865.8 |
| 2007/0294994 | A1 | | 12/2007 | Deppermann et al. | |
| 2010/0089178 | A1 | * | 4/2010 | Tragesser | A01D 43/085 73/862.627 |
| 2011/0083519 | A1 | * | 4/2011 | Barreiro | G01L 5/0038 73/862.59 |
| 2014/0301607 | A1 | * | 10/2014 | Anderson | G01N 33/0098 382/110 |
| 2016/0165799 | A1 | * | 6/2016 | Missotten | A01D 41/14 56/229 |
| 2019/0057461 | A1 | * | 2/2019 | Ruff | G01N 33/24 |
| 2019/0191631 | A1 | * | 6/2019 | Regan | G06T 7/0004 |
| 2019/0191632 | A1 | * | 6/2019 | Regan | A01G 7/00 |
| 2020/0008351 | A1 | * | 1/2020 | Zielke | A01D 45/021 |
| 2020/0267899 | A1 | * | 8/2020 | Zielke | A01D 45/021 |
| 2021/0164953 | A1 | * | 6/2021 | Robertson | G01N 3/30 |
| 2021/0329838 | A1 | * | 10/2021 | Zielke | G01B 17/00 |

FOREIGN PATENT DOCUMENTS

| DE | 102016212621 | A1 | | 1/2018 | |
|---|---|---|---|---|---|
| EP | 2965611 | A1 | * | 1/2016 | ............. A01D 34/73 |
| EP | 3391724 | A1 | * | 10/2018 | ......... A01D 34/8355 |
| EP | 3964046 | A1 | * | 3/2022 | ............. A01D 34/66 |
| WO | WO-2014160304 | A1 | * | 10/2014 | ............... A01H 1/04 |
| WO | WO-2016025848 | A1 | * | 2/2016 | ........... A01B 79/005 |
| WO | 2016205244 | A1 | | 12/2016 | |
| WO | WO-2017004074 | A1 | * | 1/2017 | ............... A01G 2/00 |
| WO | 2017172889 | A1 | | 10/2017 | |
| WO | WO-2021116802 | A1 | * | 6/2021 | ........... A01D 41/127 |

* cited by examiner

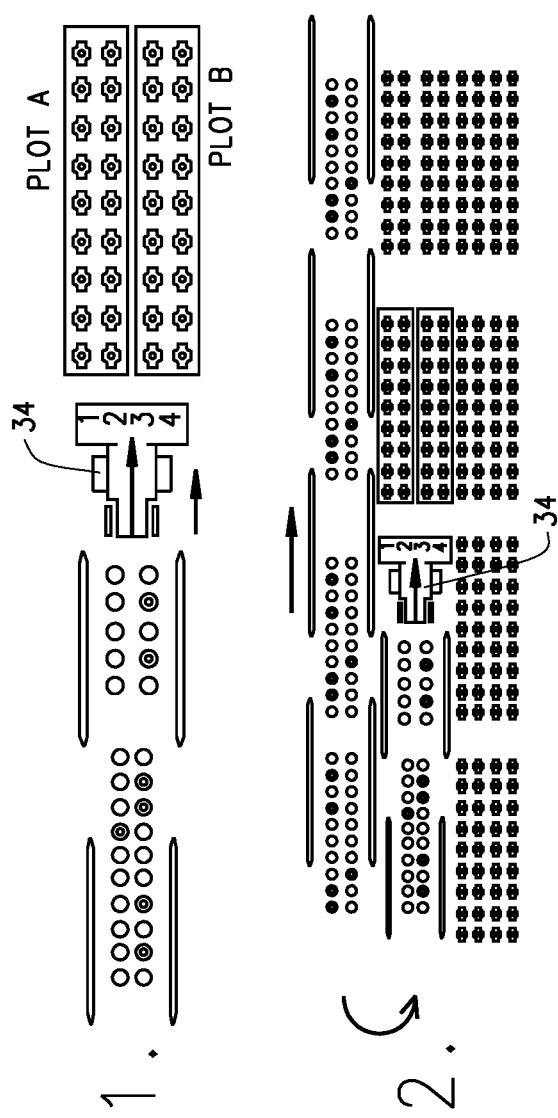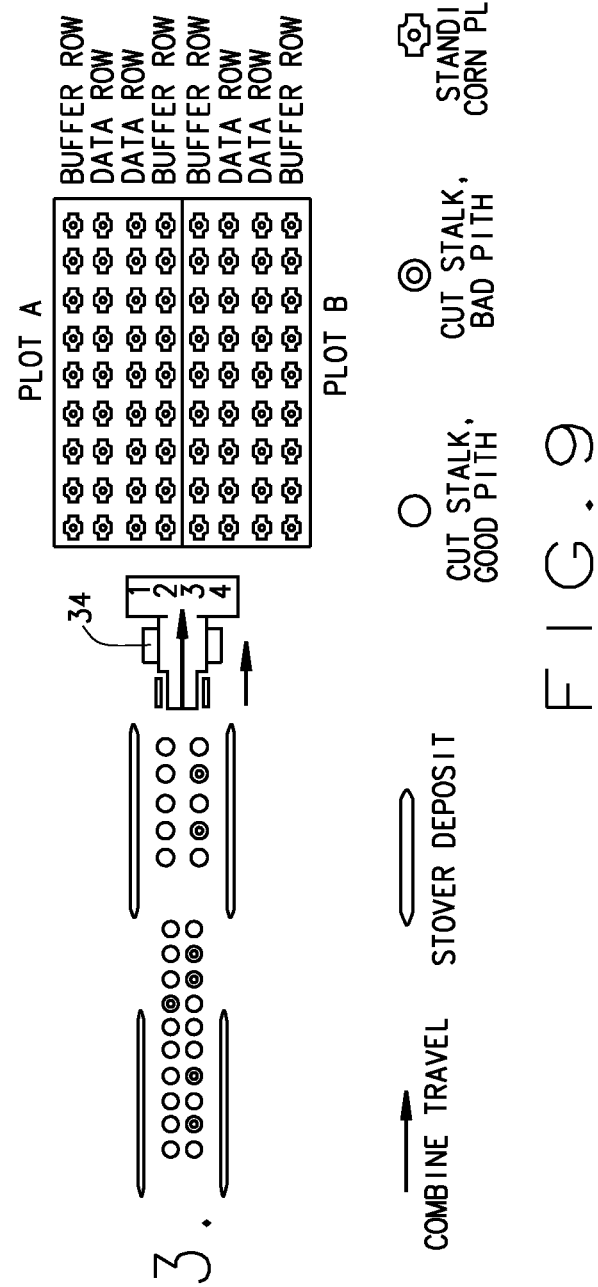
FIG. 9

RAPID STALK STRENGTH ASSESSMENT

CROSS-REFERENCE TO RELATED APPLICATIONS

This application is a National Stage of International Application No. PCT/US2019/034602, filed May 30, 2019, which claims the benefit of U.S. Patent Provisional Application No. 62/679,179 filed on Jun. 1, 2018. The disclosure of the above applications are incorporated herein by reference in their entirety.

FIELD

The present teachings relate to the testing of corn stalk strength testing for plant breeding programs, and particularly to post-harvest systems and methods for evaluating the pre-harvest strength of a corn plant stalk.

BACKGROUND

The statements in this section merely provide background information related to the present disclosure and may not constitute prior art.

Stalk strength is crucial to preventing lodging in maize (corn plants). Unfortunately, accurate and reliable scoring of stalk strength is difficult as the trait does not manifest in an external and easily visible way. A common used method to assess stalk lodging has been a field-count method where lodged plants are counted at harvest, thereby placing plants into two categories: lodged or standing. This field-count method generated stalk lodging percentages that satisfactorily served corn breeders in efforts to improve stalks by identifying germplasm most likely to lodge. However, as stalk strength of germplasm improved, additional progress using the field-count method became increasingly difficult, in part, because it is highly dependent on environmental conditions that do not occur at a frequency consistent enough to assure continued progress among germplasm with increasingly stronger stalks.

Hence, a variety of additional methods that are correlated with stalk lodging but are less affected by environmental fluctuations were evaluated and used to measure stalk strength as related to lodging potential. These methods included measures such as: breaking strength of internodes, crushing strength of excised stalks segments, thickness of stalk rind tissues, rind puncture measurements using rind penetrometers, stalk diameter measurements, internode length measurements, three-point bending and load bearing assessments, stalk flexural stiffness, elliptical section modulus, lignification of stalk tissues, density of pith tissues, water content in stalk and pith tissues, soluble solids in stalks, specific gravity of stalk tissues, stalk push tests, stalk pinch test, and assessments of fungal stalk rots. Additionally, some current methods for assessing stalk strength include sensors that are pressed against the stalk and/or devices that blow air against the stalk to determine how much force is needed to cause lodging.

Most of these methods require a laboratory and/or controlled conditions to measure the strength of stalks so the data they generate are independent of the environmental forces that affect lodging. Additionally, they require sampling of stalks during the reproductive period of grain-fill or measurements taken on stalks sampled before or at harvest. More particularly, aside from the lack of accuracy and scientific reproducibility, current methods of assessing stalk strength are based on the idea that if one desires to assess a corn stalk at the strongest point in its life cycle, it is necessary to test the stalk's strength when the plant is at that stage of its life cycle. In other words, if a breeder wants to score stalks for stalk strength, they need to conduct their stalk strength tests while the plants are growing, generally in the middle or last half of the life of the plant (e.g. while the corn plant is flowering or during grain fill). Furthermore, because current methods typically involve pressing a hand or sensor (e.g. the push test) or forcing air against the stalk until the stalk lodges and/or breaks, these methods usually kill or disrupt the plant's development so much that it is unusable for further scientific testing (e.g. collecting yield data).

SUMMARY

Plant refuse remaining in fields after a corn crop has been mechanically harvested with a combine is typically considered to be trash, and only useful as animal bedding or other purposes not directly-related to food production. There are generally two major components of corn harvest refuse: 1) plant materials such as leaves, stalks, tassels, husks, cobs, light-weighted grain, etc., that pass through the combine and are then deposited on the ground as chopped or cut pieces of various sizes after being separated from corn grain that is retained in the combine, and 2) corn stalk stumps which consists of the lower stalks and roots that pass under the combine when the combine head cuts and collects the upper portions, e.g., three-quarters, of the corn plant from which the grain is harvested. The amount and length of corn stalk stumps depends on the height at which the combine head is operated which varies within and among fields. The concept that corn stalk stumps have informational value as an alternative method to measure the potential of stalk lodging has not been realized previously, i.e., methods to assess stalk lodging have not been done utilizing post-harvest stalk stumps that remain after the combine has harvested the desired portion of the plants.

Disclosed herein is a discovery that the stalk strength of a corn plant, pre-harvest, during flowering and/or seed production, as measured by a "push test", are highly correlatable to certain types of cross-section analysis conducted post-harvest at the end of the plant's life on the discarded stalk stumps that are left in the field after harvesting (e.g., the refuse or stubble of the corn plants that is typically discarded). These methods enable accurate estimation of what a corn stalk's strength was at different points of the plant's life cycle (e.g. during grain fill) by analyzing the pith and/or rind of the stalk in cross-section after of its life cycle (e.g. post-harvest analysis of the discarded stalk stumps). Thus, plant breeders no longer need to disturb or halt a corn plant's growth and/or development with mechanized tests to score the plants for stalk strength. Rather, the plants can be allowed to mature normally, so they are still scientifically valid subjects for other experimental comparisons throughout the plant's life (e.g. yield, disease resistance, etc.).

In various embodiments, after or at substantially the same time as the corn plants have been harvested the exposed pith and/or rind of the discarded stalk stumps are viewed and/or imaged, analyzed and scored on its integrity, e.g. scored or rated based on empty spaces around the pith/rind or deterioration of the pith/rind tissue. The greater the spaces and/or deterioration of the pith/rind, that is the lower the integrity of pith/rind, the lower the resulting score will be. The scores are then translated into a stalk strength score for each plant at a pre-harvest growth stage (e.g., R6 or later), whereby a breeder can use the scores when making breeding decisions.

In various embodiments, a device or system can be used to cut the post-harvest stalk stumps growing in a field to provide a substantially clean and smooth cross-section (at any desired angle) prior to viewing and/or imaging the pith and/or rind.

Although this disclosure is not limited to certain method(s) of creating the cross-section, nor how the cross-section is scored (e.g. manually, with electronic optical/visual analysis equipment, etc.), the following are general descriptions of various exemplary embodiments.

In various embodiment, post-harvest discarded stalk stumps are cut or severed (e.g., cut or severed between the second and third internode) with a stalk stump cutter, e.g., a saw, knife, combine chopping head etc., optionally mounted to and suspended from a mobile platform that is capable of traversing the growing area (e.g., the field in which the stalk stumps have grown). The saw can be arranged on the mobile platform such that, as the mobile platform moves over or alongside a row of stalk stumps protruding out of the ground (or alternatively a row of corn plants), the stalk stump cutter rapidly cuts or severs the discarded stalk stumps (or corn plants) at substantially the same height to provide a substantially clean and smooth cross-section (at any angle), and expose the piths/rinds at a high throughput rate (e.g., 1-3 stalks per second).

In various embodiments, the discarded stalk stump cross-sections are scored by the human eye, or with an electronic camera mounted to a mobile platform capable of traversing the field. In various instances, the camera can be configured to automatically and rapidly capture images of the cross-sections of the discarded stalk stumps (e.g. 1-3 plants per second), whereafter the image data can be analyzed by a computer based data processing system that can be remotely located separate from the other components of the system, or locally located and/or combined with any one or more of the other components of the system.

In various embodiments, plant and other debris in and/or around the discarded stalk stumps can be removed to facilitate visual or image data scoring. For example, in various embodiments a blower that uses forced air to move debris away from the stalk stumps can be used, thereby providing a background of substantially bare earth substantially free of plant debris. This permits the system to more accurately distinguish the pith/rind of the stalks and improve stalk integrity assessment.

It is envisioned that the system(s) of the present disclosure can be fully-automated, capable of using electronic geo-location to perform all of the activities necessary to assess the stalk integrity of thousands or more plants per hour, thereby providing plant breeders with accurate and high-throughput system(s) and method(s) of estimating the pre-harvest stalk strength, for example during the grain fill period, for a plurality of corn plants without damaging the plants until after or during harvest. The stalk strength data obtained by the system(s) and method(s) described herein can be combined with other types of data collected about the plants' performance (e.g. yield, disease resistance) to provide plant breeders a highly-accurate, high-throughput method of assessing overall crop performance.

This summary is provided merely for purposes of summarizing various example embodiments of the present disclosure so as to provide a basic understanding of various aspects of the teachings herein. Various embodiments, aspects, and advantages will become apparent from the following detailed description taken in conjunction with the accompanying drawings which illustrate, by way of example, the principles of the described embodiments.

Accordingly, it should be understood that the description and specific examples set forth herein are intended for purposes of illustration only and are not intended to limit the scope of the present teachings.

DRAWINGS

The drawings described herein are for illustration purposes only and are not intended to limit the scope of the present teachings in any way.

Figure 3:
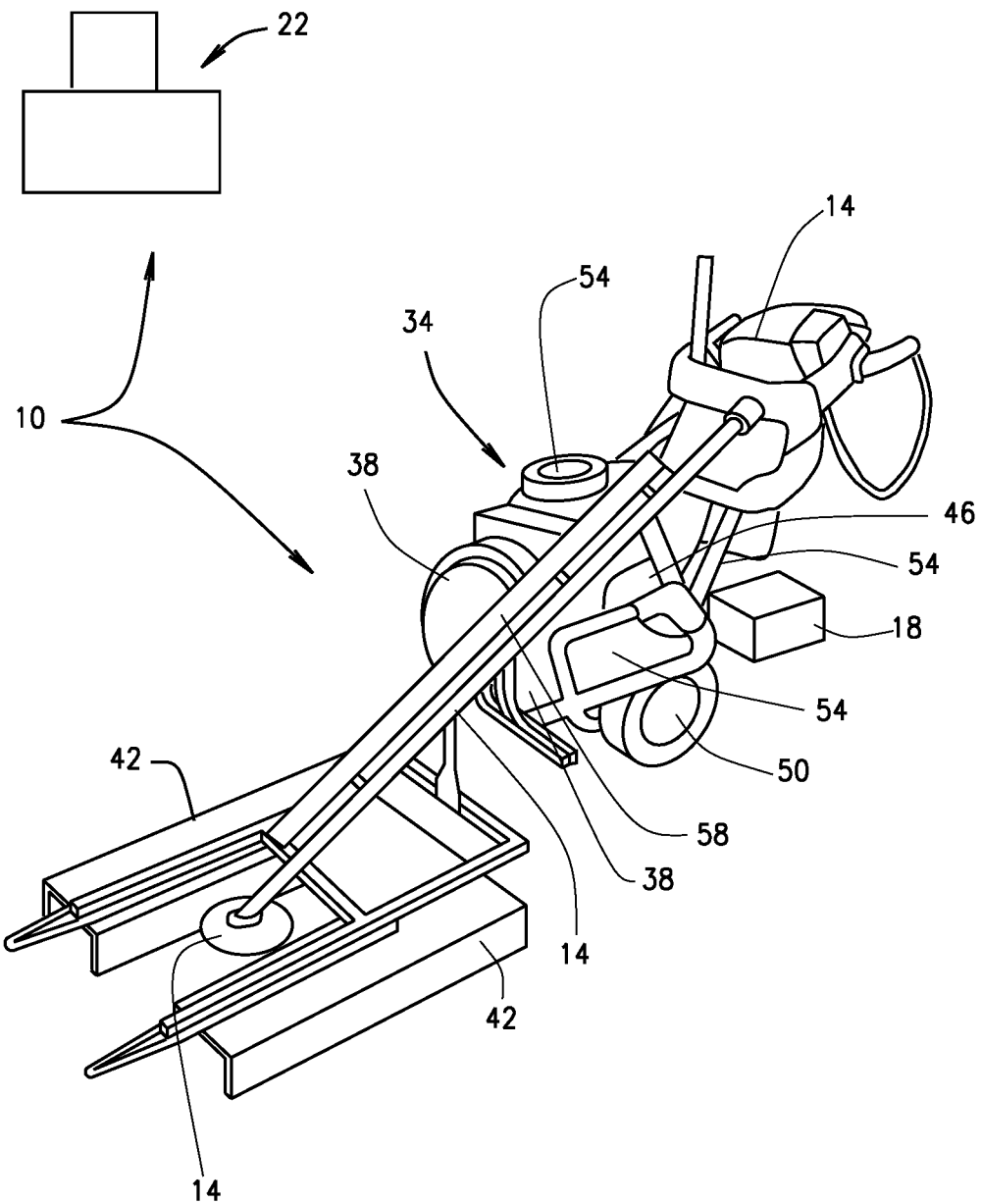
FIG. 3 is an exemplary front isometric illustration of the post-harvest stalk strength determination system shown in FIG. 1 having the various components thereof mounted to a walk-behind mobile platform, in accordance with various embodiments of the present disclosure.
Figure 8A:
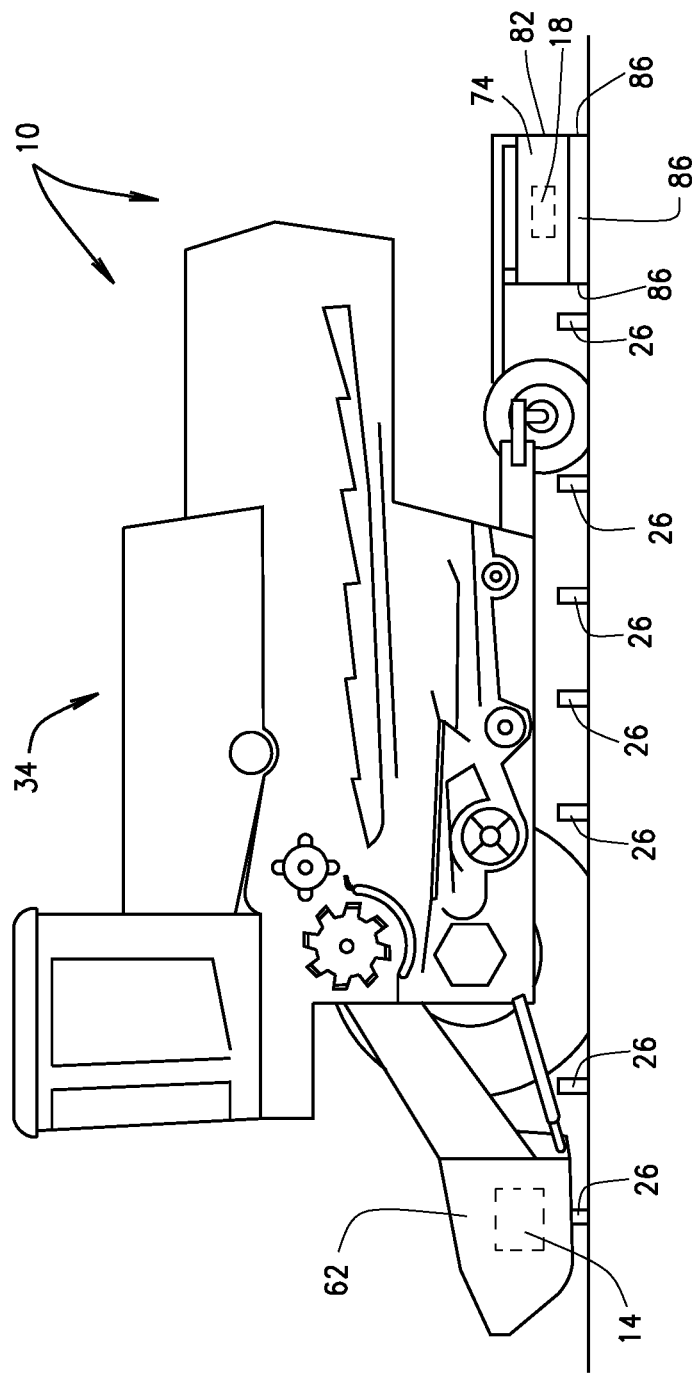
Figure 8B:
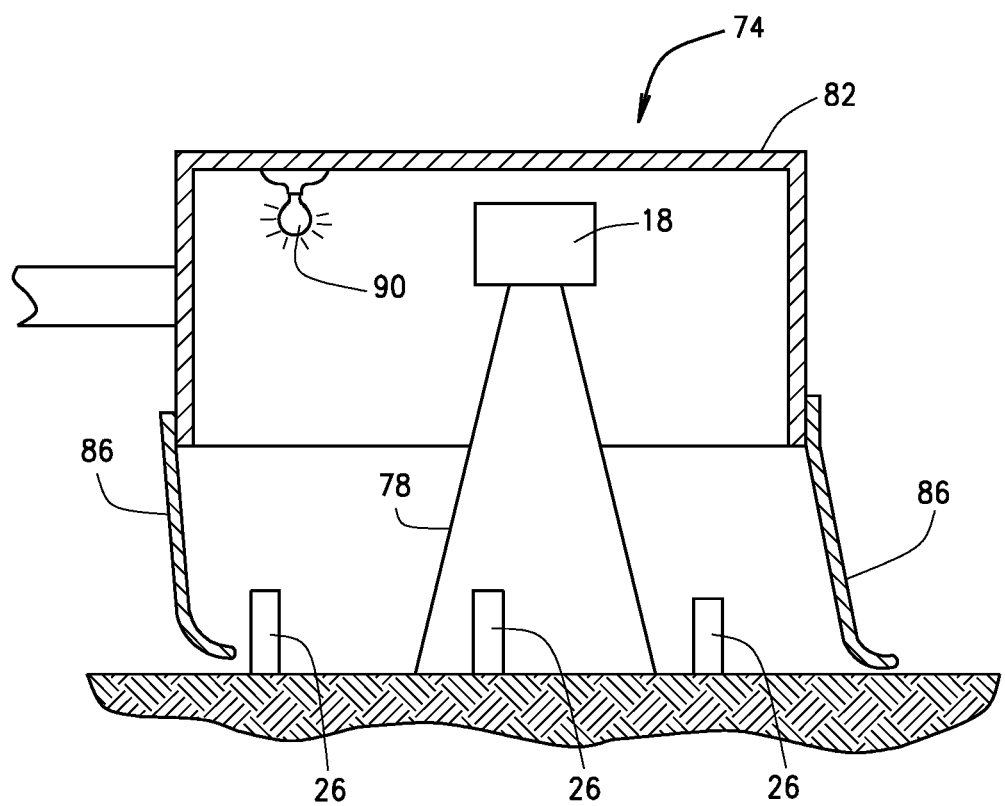

FIGS. 8A and 8B are exemplarily schematics of the post-harvest stalk strength determination system shown in FIG. 3 wherein an example sensor system capable of detecting and differentiating healthy vs. unhealthy piths of post-harvest corn stalk stumps is deployed on a combine harvester, permitting simultaneous harvest and stalk health image and/or data collection, in accordance with various embodiments of the present disclosure.

FIG. 9 exemplarily illustrates three examples of how the post-harvest stalk strength determination system show in FIGS. 1 through 3, 7 and 8 deployed on a 4-row combine harvester with onboard stalk pith-analysis capabilities, can be used to harvest research plots in a corn field at the same time it is used to collect data and/or images of corn stalk stumps, in accordance with various embodiments of the present disclosure.

Figure 10:
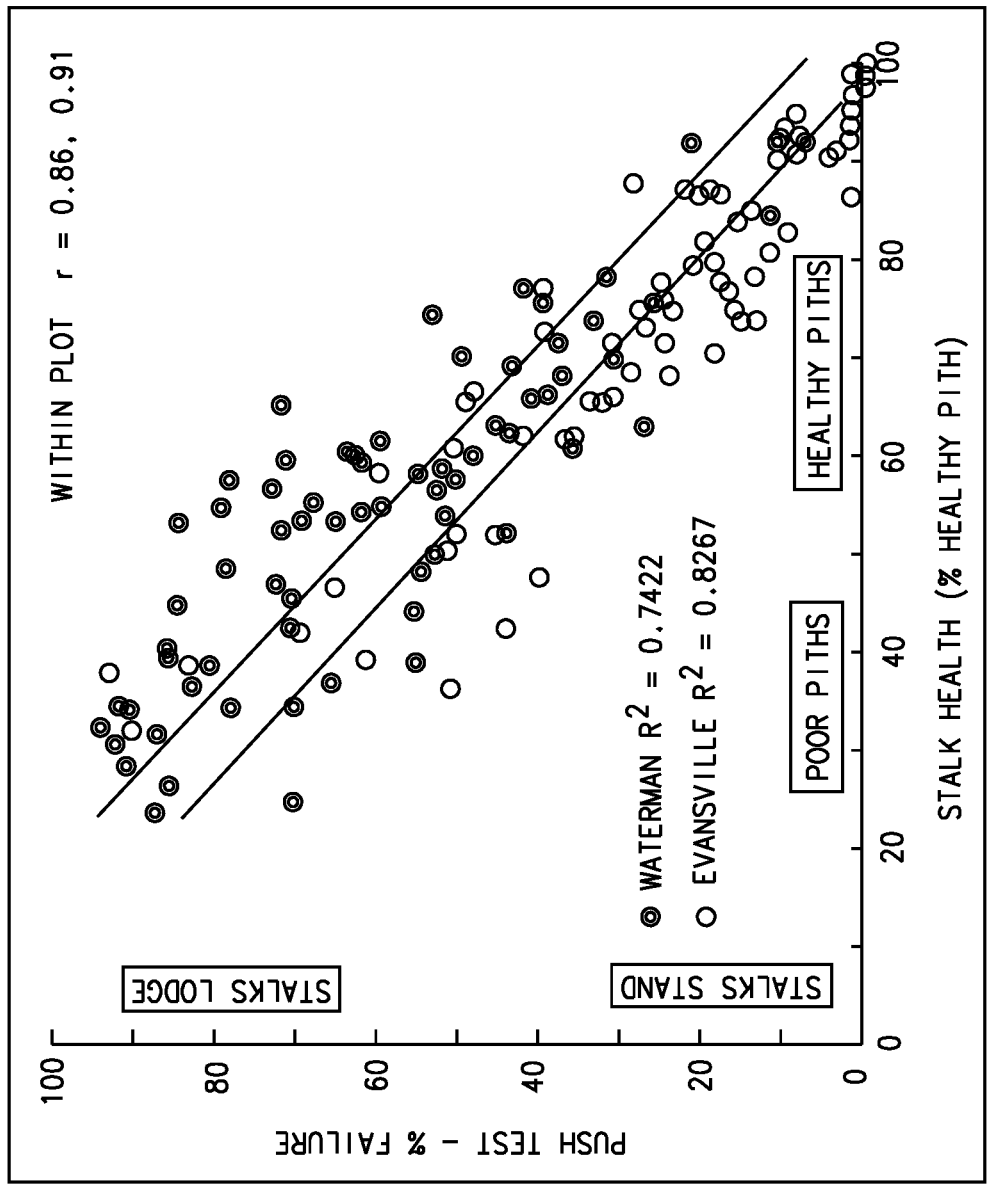

FIG. 10 exemplarily illustrates the results of a 2016 leaf-stripping-induced carbohydrate stress trials at Waterman, Illinois and Evansville, Indiana, in accordance with various embodiments of the present disclosure.

Figure 11:
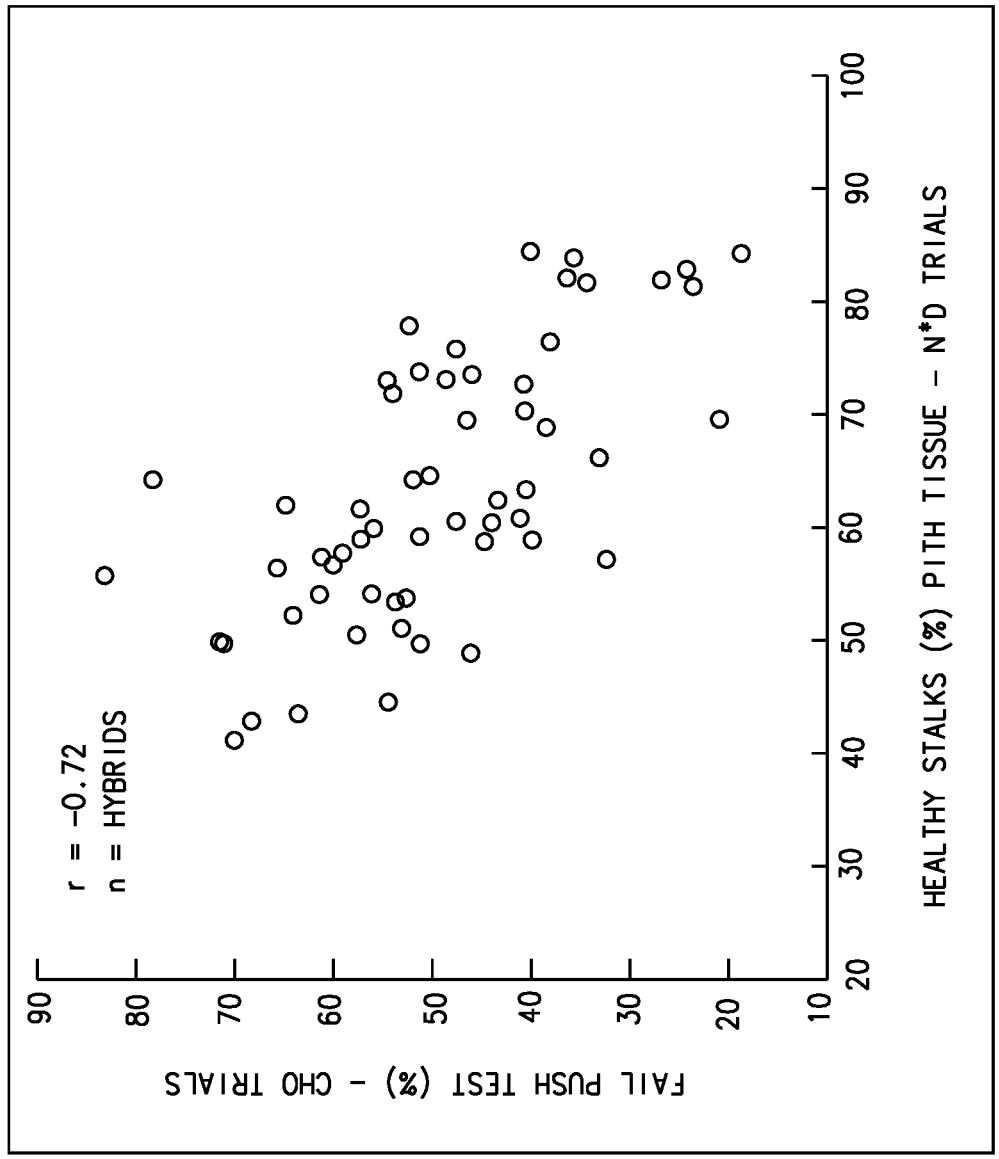

FIG. 11 exemplarily illustrates the correlations of means of the 58 hybrids common to two sets of trials in the 2016 trials at Waterman, Illinois and Evansville, Indiana, in accordance with various embodiments of the present disclosure.

Figure 12:
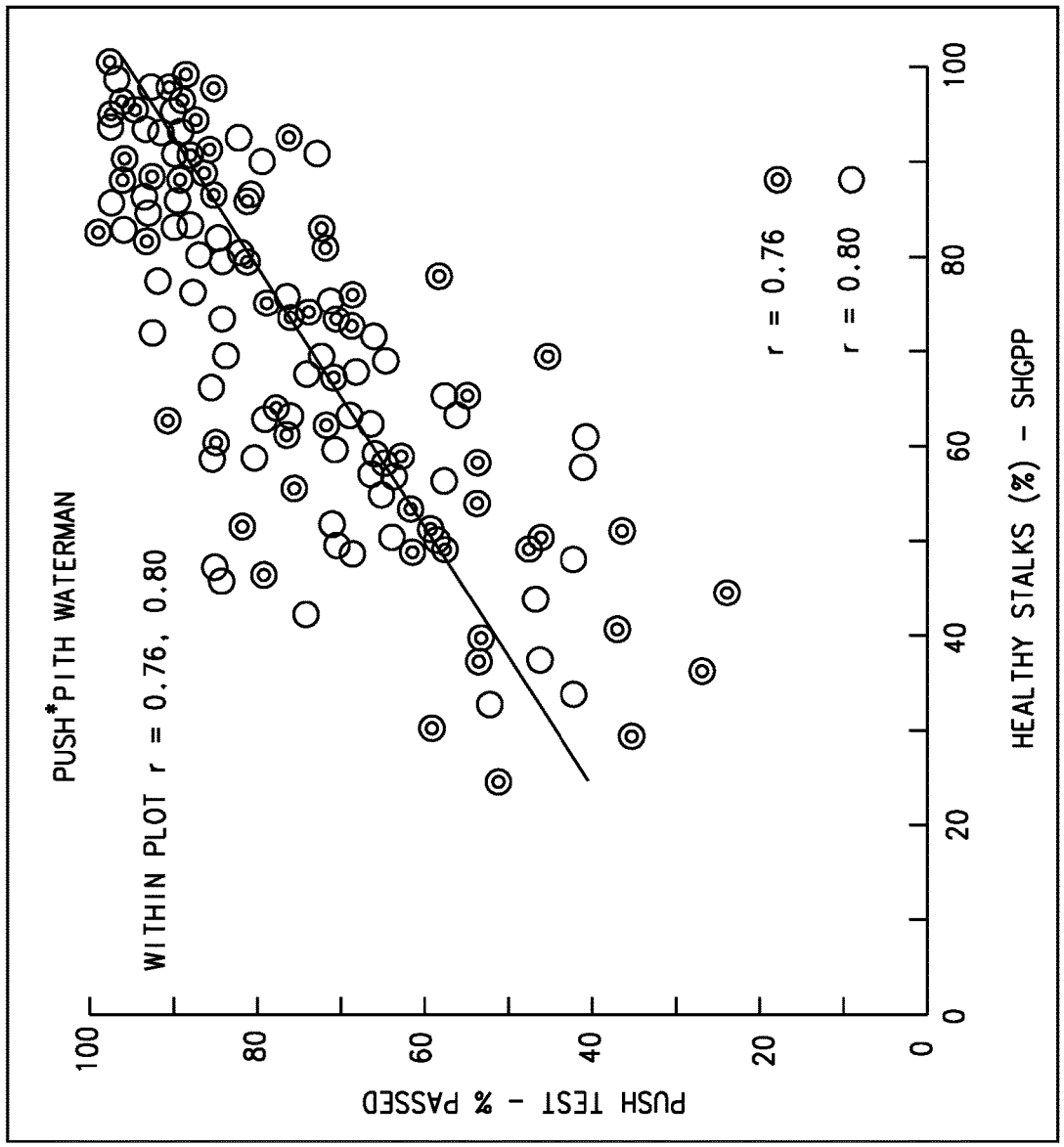

FIG. 12 exemplarily illustrates the results of a 2017 leaf-stripping-induced carbohydrate stress trials at Waterman, Illinois, in accordance with various embodiments of the present disclosure.

Corresponding reference numerals indicate corresponding parts throughout the several views of drawings.

DETAILED DESCRIPTION

The following description is merely exemplary in nature and is in no way intended to limit the present teachings, application, or uses. Throughout this specification, like reference numerals will be used to refer to like elements. Additionally, the embodiments disclosed below are not intended to be exhaustive or to limit the invention to the precise forms disclosed in the following detailed description. Rather, the embodiments are chosen and described so that others skilled in the art can utilize their teachings. As well, it should be understood that the drawings are intended to illustrate and plainly disclose presently envisioned embodiments to one of skill in the art, but are not intended to be manufacturing level drawings or renditions of final products and may include simplified conceptual views to facilitate understanding or explanation. As well, the relative size and arrangement of the components may differ from that shown and still operate within the spirit of the invention.

As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims.

Unless otherwise defined, all technical and scientific terms used herein have the same meaning as commonly understood by one of ordinary skill in the art to which this disclosure belongs. The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps can be employed.

When an element, object, device, apparatus, component, region or section, etc., is referred to as being "on," "engaged to or with," "connected to or with," or "coupled to or with" another element, object, device, apparatus, component, region or section, etc., it can be directly on, engaged, connected or coupled to or with the other element, object, device, apparatus, component, region or section, etc., or intervening elements, objects, devices, apparatuses, components, regions or sections, etc., can be present. In contrast, when an element, object, device, apparatus, component, region or section, etc., is referred to as being "directly on," "directly engaged to," "directly connected to," or "directly coupled to" another element, object, device, apparatus, component, region or section, etc., there may be no intervening elements, objects, devices, apparatuses, components, regions or sections, etc., present. Other words used to describe the relationship between elements, objects, devices, apparatuses, components, regions or sections, etc., should be interpreted in a like fashion (e.g., "between" versus "directly between," "adjacent" versus "directly adjacent," etc.).

As used herein, the term "and/or" includes any and all combinations of one or more of the associated listed items. For example, A and/or B includes A alone, or B alone, or both A and B.

Although the terms first, second, third, etc. can be used herein to describe various elements, objects, devices, apparatuses, components, regions or sections, etc., these elements, objects, devices, apparatuses, components, regions or sections, etc., should not be limited by these terms. These terms may be used only to distinguish one element, object, device, apparatus, component, region or section, etc., from another element, object, device, apparatus, component, region or section, etc., and do not necessarily imply a sequence or order unless clearly indicated by the context.

Moreover, it will be understood that various directions such as "upper", "lower", "bottom", "top", "left", "right", "first", "second" and so forth are made only with respect to explanation in conjunction with the drawings, and that components may be oriented differently, for instance, during transportation and manufacturing as well as operation. Because many varying and different embodiments may be made within the scope of the concept(s) herein taught, and because many modifications may be made in the embodiments described herein, it is to be understood that the details herein are to be interpreted as illustrative and non-limiting.

The apparatuses/systems and methods described herein can be implemented at least in part by one or more computer program products comprising one or more non-transitory, tangible, computer-readable mediums storing computer programs with instructions that may be performed by one or more processors. The computer programs may include processor executable instructions and/or instructions that may be translated or otherwise interpreted by a processor such that the processor may perform the instructions. The computer programs can also include stored data. Non-limiting examples of the non-transitory, tangible, computer readable medium are nonvolatile memory, magnetic storage, and optical storage.

As used herein, the term module can refer to, be part of, or include an application specific integrated circuit (ASIC); an electronic circuit; a combinational logic circuit; a field programmable gate array (FPGA); a processor (shared, dedicated, or group) that performs instructions included in code, including for example, execution of executable code instructions and/or interpretation/translation of uncompiled code; other suitable hardware components that provide the described functionality; or a combination of some or all of the above, such as in a system-on-chip. The term module can include memory (shared, dedicated, or group) that stores code executed by the processor.

The term code, as used herein, can include software, firmware, and/or microcode, and can refer to one or more programs, routines, functions, classes, and/or objects. The term shared, as used herein, means that some or all code from multiple modules can be executed using a single (shared) processor. In addition, some or all code from multiple modules can be stored by a single (shared) memory. The term group, as used above, means that some or all code from a single module can be executed using a group of processors. In addition, some or all code from a single module can be stored using a group of memories.

As used herein, a test plot will be understood to mean a single field, or one of a plurality plots within a research field that has been subdivided into a plurality of plots. Each test plot typically comprises one or more rows of plants comprising from about 5 to about 15 or 20 plants in each row, wherein the plants are subject to various crop breeding and analytics research procedures and tests for developing various strains, hybrids, genotypes, etc. of plants. For example, test plots in a growing area can receive certain treatments (e.g. chemical applications to the plants and/or growing environment), and/or can comprise plants of certain genetics, and/or combinations thereof. Each test plot within a field is purposely separated from other test plots by a gap, or alleys, where no plants are grown. The gaps or alleys maintain the identity of the plant material within each respective test plot. Hence, there are typically many alleys in a research field, often comprising 10-30 feet of space with no plants.

As used herein, a microbe will be understood to be a microorganism, i.e. a microscopic living organism, which can be single celled or multicellular. Microorganisms are very diverse and include all the bacteria, archea, protozoa, fungi, and algae, especially cells of plant pathogens and/or plant symbiots. Certain animals are also considered microbes, e.g. rotifers. In various embodiments, a microbe can be any of several different microscopic stages of a plant or animal. Microbes also include viruses, viroids, and prions, especially those which are pathogens or symbiots to crop plants.

As used herein the term plant refers to a whole plant, any part thereof, or a cell or tissue culture derived from a plant, comprising any of: whole plants, plant components or organs (e.g., leaves, stems, roots, etc.,), plant tissues, seeds, plant cells, and/or progeny of the same. A plant cell is a biological cell of a plant, taken from a plant or derived through culture from a cell taken from a plant.

As used herein the term fungus refers to a whole fungus, any part thereof, or a cell or tissue culture derived from a fungus, comprising any of whole fungus, fungus components or organs, fungal tissues, spores, fungal cells, including cells of hyphae and/or cells of mycelium, and/or progeny of the same. A fungus cell is a biological cell of a fungus, taken from a fungus or derived through culture from a cell taken from a fungus.

As used herein the phrase population of plants or plant population means a set comprising any number, including one, of individuals, objects, or data from which samples are taken for evaluation, e.g. estimating QTL effects and/or disease tolerance. Most commonly, the terms relate to a breeding population of plants from which members are selected and crossed to produce progeny in a breeding program. A population of plants can include the progeny of a single breeding cross or a plurality of breeding crosses, and can be either actual plants or plant derived material, or in silico representations of the plants. The population members need not be identical to the population members selected for use in subsequent cycles of analyses or those ultimately selected to obtain final progeny plants. Often, a plant population is derived from a single biparental cross, but can also derive from two or more crosses between the same or different parents. Although a population of plants can comprise any number of individuals, those of skill in the art will recognize that plant breeders commonly use population sizes ranging from one or two hundred individuals to several thousand, and that the highest performing 5-20% of a population is what is commonly selected to be used in subsequent crosses in order to improve the performance of subsequent generations of the population.

Figure 1:
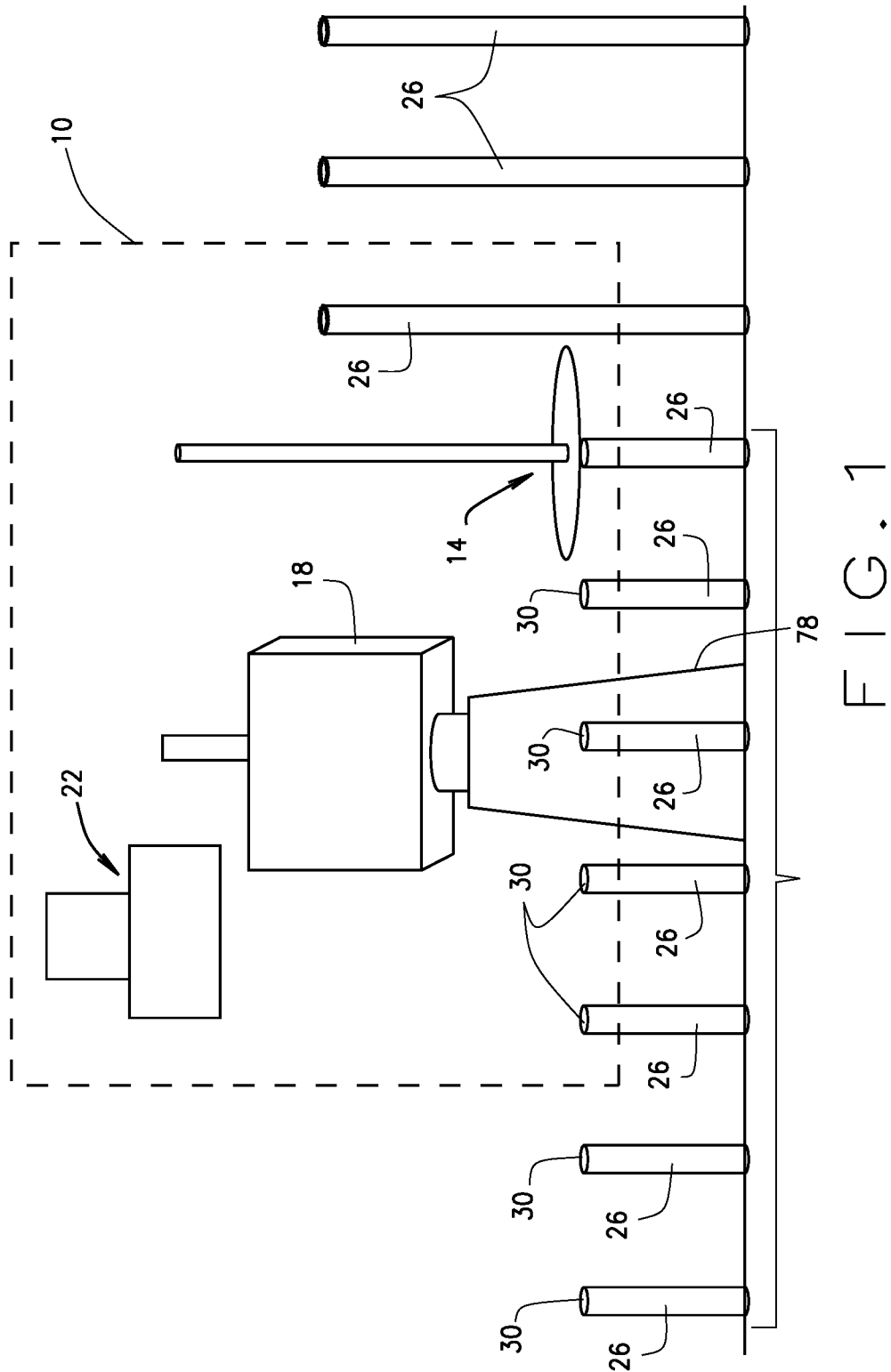
FIG. 1 is a schematic of a post-harvest stalk strength determination system, in accordance with various embodiments of the present disclosure.

Referring now to FIG. 1, the present disclosure generally provides systems and methods for post-harvest determination of pre-harvest strength of a corn stalk. That is, the present disclosure generally provides systems and methods for determining the strength of corn stalks at a desired growth stage, e.g., growth stage R4, R5, R6, black layer, etc., after the corn stalks have been severed and the corn plants have been harvested. Implementation of the systems and methods of the present disclosure allow the corn plants to grow to maturity, or until harvested, without being damaged because the stalk strength analysis and determination is performed on the discarded stalk stumps that remain rooted in the ground in the field after harvest of the corn plants.

As used herein, it should be understood that post-harvest stalk stumps refer to the discarded stalk stumps that remain rooted in the ground in the field after harvest of the corn plants, and that the method and systems described herein are utilized and implemented on such discarded stalk stumps that remain rooted in the ground in the field after harvest of the corn plants.

In various embodiments, the present disclosure provides a post-harvest stalk strength determination system 10 for determining stalk strength at any desired growth stage prior to harvest that generally comprises at least one stalk stump cutter 14, at least one imaging device 18 and at least one computer based data processing system 22. Although the system 10 can include a plurality of stalk stump cutters 14 and/or a plurality of imaging devices 18 and/or a plurality of data processing systems 22, for simplicity and conciseness the system 10 will be described herein as comprising a single stalk stump cutter 14, a single imaging device 18, and a single data processing system 22. In various embodiments, the stalk stump cutter 14 can be structured and operable to cut, at any desired angle, a discarded post-harvest stalk stump 26 to provide a substantially flat and even cross-sectional surface 30 (often referred to herein simply as the cross-section 30) of the stalk stump 26. The stalk stump cutter 14 can be any device operable to cut or sever discarded post-harvest stalk stumps 26 such that a substantially flat even cross-section 30 is provided. For example, in various instances the stalk stump cutter 14 can comprise a discus saw blade (similar to a hand-held power saw blade) and a motor that spins the discus saw blade to cut the post-harvest stalk stumps 26 to provide the prepared cross-sections 30. In other instances, the stalk stump cutter 14 can comprise an automated scissor device that slices through the post-harvest stalk stumps 26 to provide the prepared cross-sections 30. Alternatively, the stalk stump cutter 14 can comprise one or more spinning knife blade (similar to a lawn mower blade) and a motor that spins the knife blade to sever the post-harvest stalk stumps 26 to provide the prepared cross-sections 30.

It is envisioned that in various embodiments, the stalk stump cutter 14 can comprise a combine chopping head that is structured and operable to cut the corn plants such that the discarded stalk stump that remains has a substantially flat even cross-section.

In various instances, the imaging device 18 is structured and operable to acquire image data of the stalk stump cross-section, and the computer based data processing system 22 is structured and operable to analyze the image data and determine a pre-harvest (e.g., prior to harvest) or at harvest (e.g., during harvest) stalk strength of the corresponding plant stalk. The imaging device 18 can be any imagining device or sensor suitable to gather desired image data of each prepared stalk stump cross-section 30, such as charged coupled device (CCD) camera, an infrared (IR) camera, a high resolution digital camera, or any other suitable imaging device.

As used herein a post-harvest corn stalk stump 26 will be understood to mean the portion of a corn stalk extending from the ground after the stalk has been cut by a harvesting machine, e.g., a corn harvester, to harvest the corn of the respective stalk. More specifically, as used herein a post-harvest corn stalk stump 26 is the discarded stalk stump and left behind in the field as refuse to be tilled into the soil the next planting season. Discarded post-harvest stalk stumps 26 that have been cut by the stalk stump cutter 14 and have substantially flat and even cross-sections 30 will be referred to herein as being 'prepared' stalk stumps 26.

The data processing system 22 can be any computer or processor based system or device suitable for electronically communicating (wired or wirelessly) with the stalk stump cutter 14 and/or the imaging device 14 to receive image data from the imaging device 18, and/or control the operation of the imaging device 18, and/or receive operational data from the stalk stump cutter 14, and/or control operation of the stalk stump cutter 14, and process and analyze the image data to determine a pre-harvest stalk strength of the respective corn stalk. Particularly, in various instances, the data processing system 22 is structured and operable to process and analyze the image data to determine the stalk strength of the respective stalk at a desired growth stage of the respective corn plant, e.g., growth stage R4, R5, R6, black layer, etc. It is envisioned that the computer based data processing system 22 can comprise any combination of a general-purpose computer, any other computer based system or device, and one or more application specific integrated circuits (ASICs), electronic circuits, combinational logic circuits, field programmable gate arrays (FPGA), or other hardware components that provide various functionality of the system 10, as described herein. Furthermore, the data processing system 22 can be a single component or multiple components that are located locally on/at the system 10 or remotely from the system 10, or a combination thereof.

Figure 6:
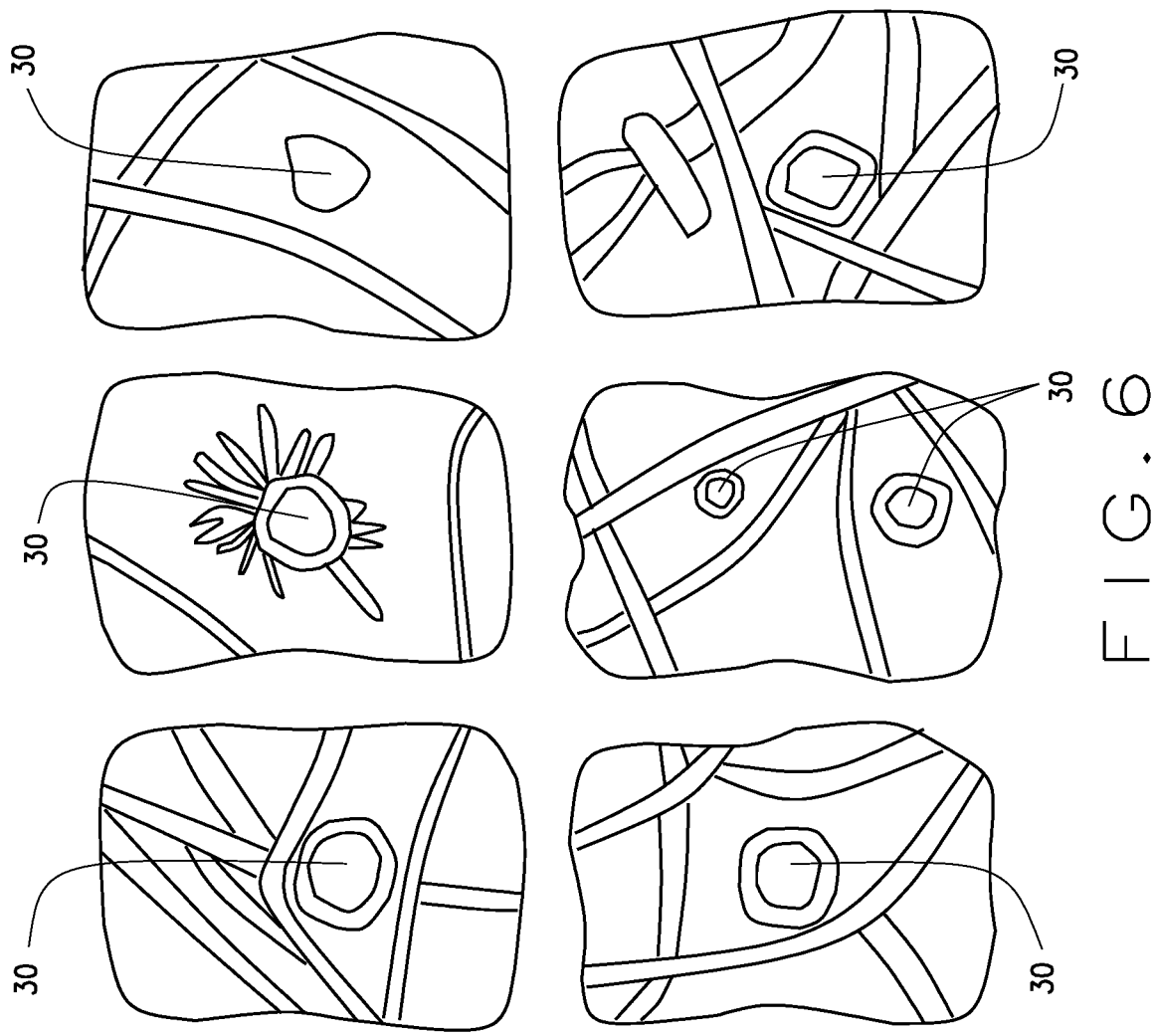
FIG. 6 is an exemplary illustration of a plurality of substantially flat and even prepared cross-sections of various stalk stumps provided using the post-harvest stalk strength determination system shown in FIGS. 1 through 3, in accordance with various embodiments of the present disclosure.

Furthermore, in various embodiments, one or more of the components of the system 10, e.g., the stalk stump cutter 14, the imaging device 18, the data processing system, and all other components of the system 10 described herein can be standalone units such that they are not interconnected or mounted to a common structure, and can be utilized independently in separate sequential phases. For example, in various instances the stalk stump cutter 14, the imaging device 18 and the data processing system 22 can each be an independent standalone unit wherein the stalk stump cutter 14 is carried, pushed, pulled, or driven through a plot and used to prepare (e.g., cut) a plurality of or all of the stalk stumps 26 in the plot such that a plurality or all the respective stalk stumps 26 have a substantially flat and even cross-section 30, as a first step or process. It should be understood that the stalk stump cutter 14 can cut the respective stalk at any angle (e.g., 90°, 45°, 30°, etc.) relative to the length of the plant stalk (e.g., a longitudinal axis of the plant stalk) such that a substantially flat and even cross-sectional surface 30 is provided. In various instances, the stalk stumps 26 are cut (e.g., prepared) between the second and third internodes. Subsequently, in various instances, the stalk stump cutter 14 is set aside and the imaging device 18 can be carried, pushed, pulled, or driven through the plot and used to capture image date of each respective stalk stump flat and even cross-section 30, and communicate the captured image data to the data processing system 10, as a second step or process. Thereafter, the imaging device 18 is set aside and the data processing system 22, located remotely or separately from the stalk stump cutter 14 and the imaging device 18 processes and analyzes, via execution of one or more stalk strength algorithms, the captured image data for each stalk stump cross-section 30 and determines a stalk strength value for each stalk stump 26 at a desired pre-harvest growth stage of the respective corn plants. For example, in various embodiments the image data can be assayed to determine the color of the tissue in a pith region of the stalk stump cross-section 30 (as exemplarily illustrated in FIG. 6).

It is envisioned that in various embodiments, the system and method do not include the imaging device 18 or the data processing system 22. In such instances, once the discarded stalk stumps 26 have been prepared by the stalk stump cutter 14, which in various embodiments can be a chopping head within the harvesting head(s) 62 of a corn harvester or corn harvesting combine, manual visual data can be collected and recorded (recorded manually or electronically) by one or more data collecting person in the field, and subsequently analyzed by one or more data analysis person.

In various other instances, one or more of the components of the system 10, e.g., the stalk stump cutter 14, the imaging device 18, the data processing system, and all other components of the system 10 described herein, can be mounted to a common structure or chassis such as a mobile platform 34 exemplarily illustrated in FIGS. 3, 4, 5 and 7. In such instances, the stalk stump cutter 14 can be mounted forward of the imaging device 18 on the mobile platform 34 (e.g., the common structure or chassis) and the mobile platform 34 can be pushed, pulled, or driven through the plot such that, as the mobile platform 34 traverses a row of discarded stalk stumps, the stalk stump cutter 14 prepares (e.g., cuts) each discarded stalk stump 26 and thereafter the imaging device 18 collects the image data of the respective stalk stump cross-sections 30. In such instances, the stalk stump cutter 14 can be positioned on the mobile platform 34 a distance from the imaging device 18 such that one or more (e.g., 1, 2, 3 or 4) discarded stalk stumps 26 are prepared (e.g., cut) by the stalk stump cutter 14 before the imaging device 18 passes over the prepared discarded stalk stumps 26 to collect the image data of the respective cross-sections 30. For example, the stalk stump cutter 14 can be positioned on the mobile platform 34 a distance from the imaging device 18 such that a first and a second stalk stump 26 will be prepared (e.g., cut) and the first stalk stump cross-section 30 will not be imaged by the imaging device 18 until after the second stalk stump 26 is prepared (e.g., cut). In various instances, the stalk stumps 26 are cut (e.g., prepared) between the second and third internodes.

Again, it is envisioned that in various embodiments, the stalk stump cutter 14 can be a chopping head within one or more corn harvesting head(s) 62 that cut(s) mature corn plants to harvest the corn plants leaving behind discarded stalk stump 26 that have been prepared by the harvesting combine harvesting head(s) 62 to have substantially flat and even cross-sectional surface 30.

Figure 2:
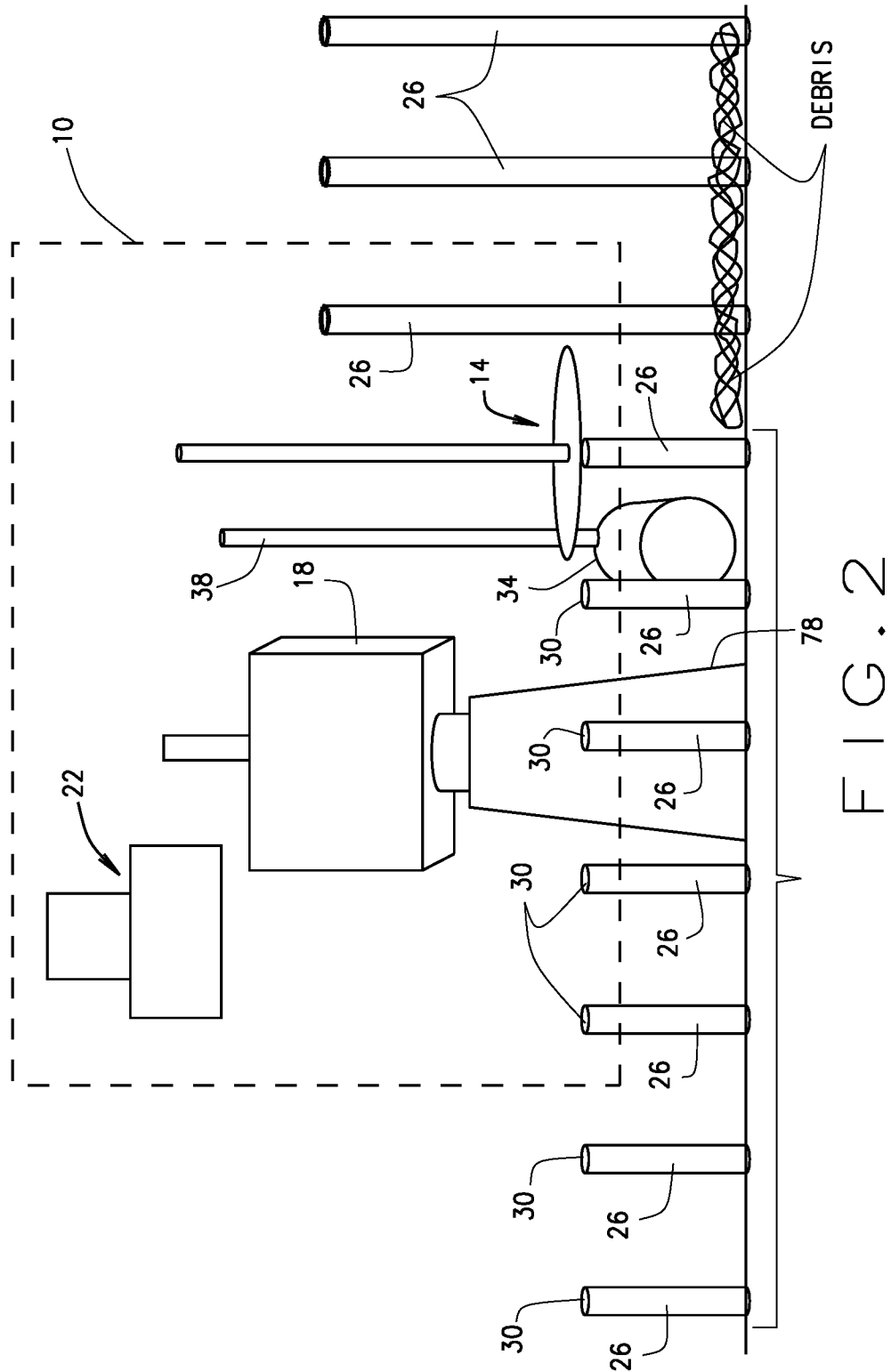
FIG. 2 is a schematic of the post-harvest stalk strength determination system shown in FIG. 1, in accordance with various other embodiments of the present disclosure.

Referring now to FIG. 2, in various embodiments, the system 10 can further include a debris dispersion device 38 that is structured and operable to disperse or remove any debris from around each cut stalk stump 26 prior to imaging of the prepared stalk stumps 26. The debris can include such things as twigs, leaves, splinters, chunks, pieces, or remnants of the corn plants and/or stalks that result from harvesting of the corn plants and/or preparing (e.g., cutting) of the stalk stumps 26 by the stalk stump cutter 14. By dispersing or removing of the debris from around the stalk stumps 26 prior to imaging thereof, the image data of each stalk stump cross-section 30 collected manually/visual or by the imaging device 18 will not include and be substantially free of data representative of any such debris surrounding the respective stalk stump 26, e.g., the image data will not be cluttered with data representative of any such debris, thereby making analysis of the acquired image data manually or by the data processing system 22 easier and more accurate. Accordingly, prior to manually viewing or passing the imaging device 18 over the tops of the prepared stalk stumps 26 to collect image data of the cross-sections 30, the debris dispersion device 38 will clear the ground surrounding the base of respective stalk stump(s) 26 of debris (e.g., disperse or remove the debris from the ground surrounding the base of the respective stalk stumps 26) so that clean, clear, uncluttered image data of the respective cross-sections 30 can be obtained. The debris dispersion device 38 can be any device structure and operable to disperse or remove debris on the ground around the stalk stumps 26 such as a broom, brush, rack, vacuum device or blower device. In various embodiments, as exemplarily shown in 3, 4 and 5 the debris dispersion device 38 can be a blower device operable to generate a stream of air that can be directed toward the ground at the base of stalk stumps 26 to disperse or blow away debris surrounding the base of the stalk stumps 26.

As described above, in various embodiments one or more of the components of the system 10 can be standalone units such that they are not interconnected or mounted to a common structure, and can be utilized independently in separate sequential phases or operations. In such embodiments, wherein the system 10 includes the debris dispersion device 38, after the stalk stumps 26 have been prepared using the stalk stump cutter 14 in a first step or process, the debris dispersion device 38 can be carried, pushed, pulled, or driven through a plot and used to disperse or remove the debris from around at least the base of each stalk stump 26, as a second step or process. Thereafter, in various instances, the imaging device 18 can be carried, pushed, pulled, or driven through the plot and used to capture image date of each respective stalk stump flat and even cross-section 30 and communicate the captured image data to the data processing system 10, as a third step or process. As also described above, in various instances, wherein the data processing system 22 is located remotely or separately from the stalk stump cutter 14, the debris dispersion device 38 and the imaging device 18, the data processing system 22 processes and analyzes, via execution of one or more stalk strength algorithms by one or more processor of the data processing system 22, the captured image data for each stalk stump cross-section 30 and determines a stalk strength value for each stalk stump 26 at a desired pre-harvest growth stage of the respective corn plants (e.g., R4, R5, R6 or black layer).

As also described above, in various embodiments, one or more of the components of the system 10 can be mounted to a common structure or chassis such as a mobile platform 34 exemplarily illustrated in FIGS. 3, 4, 5 and 7. In such instances, wherein the system 10 includes the debris dispersion device 38, the stalk stump cutter 14 can me mounted forward of the imaging device 18 on the mobile platform 34 and the debris dispersion device 38 can be mounted between the stalk stump cutter 14 and the imagining device 18. In operation, the mobile platform 34 can be pushed, pulled, or driven through the plot such that, as the mobile platform 34 traverses a row of stalk stumps 26, the stalk stump cutter 14 prepares (e.g., cuts) each stalk stump 26. Subsequently, in various instances, as the mobile platform continues along the row, and prior to acquisition of the image data, the debris dispersion device 38 is passed in close proximity to the base of each prepared stalk stump 26 to disperse or remove any debris around the base(s) of the respective prepared stalk stump(s) 26. Thereafter, in various instances, as the mobile platform continues along the row, the imaging device 18 passes over each prepared stalk stump 26 that has had the debris dispersed or removed from its base and collects the image data of the respective stalk stump cross-sections 30. In such instances, the stalk stump cutter 14 can be positioned on the mobile platform 34 a distance from the imaging device 18 such that one or more (e.g., 1, 2, 3 or 4) stalk stumps 26 are prepared (e.g., cut) by the stalk stump cutter 14, and the debris is cleared from around the respective bases before the imaging device 18 passes over the prepared stalk stumps 26 to collect the image data of the respective cross-sections 30. For example, the stalk stump cutter 14 can be positioned on the mobile platform 34 a distance from the imaging device 18 such that a first and a second stalk stump 26 will be prepared (e.g., cut), and the debris cleared from around their bases, and the first stalk stump cross-section 30 will not be imaged by the imaging device 18 until after the second stalk stump 26 is prepared (e.g., cut).

It is envisioned that the mobile platform 34 can be manually propelled, or automatically propelled, (e.g., propelled by a motor or engine) and can be a walk-behind platform (such as that shown in 3, 4 and 5) or riding platform (e.g., a tractor or a corn harvester modified to have the components of system 10 mounted thereto). It is envisioned that in various embodiments the mobile platform can be an unmanned vehicle whose movement and activities are controlled by automated systems. In the embodiments wherein the components of system 10 are mounted to a mobile platform 34, in general operation, in various instances, after a field or plot (e.g., test plot) of corn plants have been harvested such that all that remains of the corn plants is their respective discarded post-harvest stalk stumps 26, the mobile platform 34 having the components of the system 10 mounted thereon is traversed (e.g., manually motivated/propelled or automatically motivated/propelled) down or along a first row of stalk stumps 26. As the mobile platform 34 travels down the row of post-harvest stalk stumps 26 are aligned with the stalk stump cutter 14 such that the stalk stump cutter 14 prepares (e.g., cuts, slices, or severs and any desired angle) the stalk stumps 26 to provide a substantially flat and even cross-section 30 for each prepared stalk stump 26. In various instances the stalk stump cutter 14 cuts (e.g., prepares) each stalk stump 26 at substantially the same height (e.g., between the second and third internode) so that the image data acquired for each stalk stump cross-section 30 is consistent and representative of the same stalk strength data for each stalk stump 26, thereby enhancing the accuracy of the analysis of the image data and the resulting pre-harvest stalk strength determinations.

After one or more of the stalk stumps 26 have been prepared by the stalk stump cutter 14, and the mobile platform 34/system 10 advances down the row, in various instances, the imaging device 18 is sequentially passed over each prepared stalk stump 26 and collects image data of the substantially flat and even cross-section 30 of each prepared stalk stump 26. Simultaneously or subsequently, the imaging device 18 sends the collected image data to data processing system 22. In such instances, the data processing system 22 executes one or more stalk strength algorithm on the collected image data for each prepared stalk stump 26 to determine a pre-harvest stalk strength for each respective stalk stump 26. As described above, the collected image data can be utilized to determine the pre-harvest stalk strength for each stalk stump 26 at any desired growth stage of the corn plants, such as R4, R5, R6, black layer, etc. Particularly, in various embodiments, the data processing system 22 can analyze the collected image data and provide a score or an index value indicative of the desired growth stage stalk strength for each respective stalk stump 26. More particularly, the data processing system 22 assays the image data to determine the amount of damaged or missing tissue in a pith region of the stalk stump cross-section and assigns a particular score or index number (e.g., a number between 1 and 10) that indicates the stalk strength of the respective stalk at the desired pre-harvest growth stage. That is, the data processing system 22 assigns a post-harvest score or index number to each stalk stump 26 based on the assay, wherein the score or index number corresponds to the pre-harvest stalk strength of the respective corn plant at the desired growth stage, e.g., R4, R5, R6, black layer, etc. As described above, in various embodiments, the image data can be assayed to determine the color of the tissue in a pith region of the stalk stump cross-section 30, wherein such color data can be utilized to post-harvest determine various aspects of the pre-harvest stalk health.

As described above, in various embodiments, once the stalk stumps 26 have been prepared, the image data can be manually visually collected. Additionally, in such embodiments, the manually visually collected image data can be manually analyzed or entered into a data processing system (e.g., data processing system 22) and analyzed via execution of one or more stalk strength algorithm.

In the embodiments wherein the system 10 includes the debris dispersion device 38, as the mobile platform 34/system 10 advances down the row, subsequent to the preparation of a respective stalk stump 26 and prior to the collection of the image data thereof, the debris dispersion device 38 disperses or removes the debris from around the base of one or more of the prepared stalk stumps 26 so that the collected image data of each substantially flat and even cross-section 30 is uncluttered with background data of the debris. The process above is repeated on each row of stalk stumps 26 for which the pre-harvest stalk strength analysis is desired.

Figure 4:
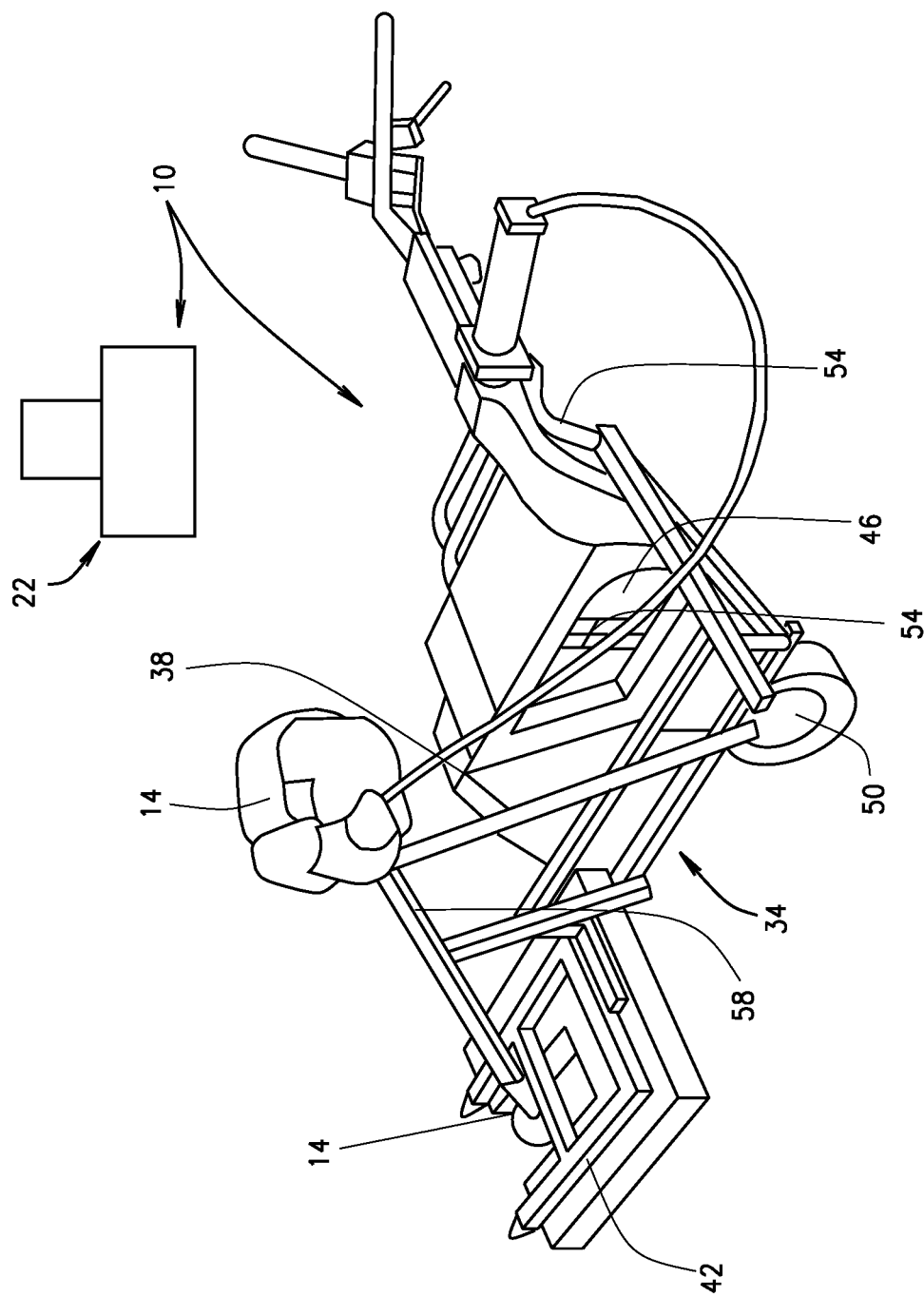
FIG. 4 is an exemplary rear isometric illustration of the post-harvest stalk strength determination system shown in FIG. 3 having the various components thereof mounted to a walk-behind mobile platform, in accordance with various embodiments of the present disclosure.
Figure 5:
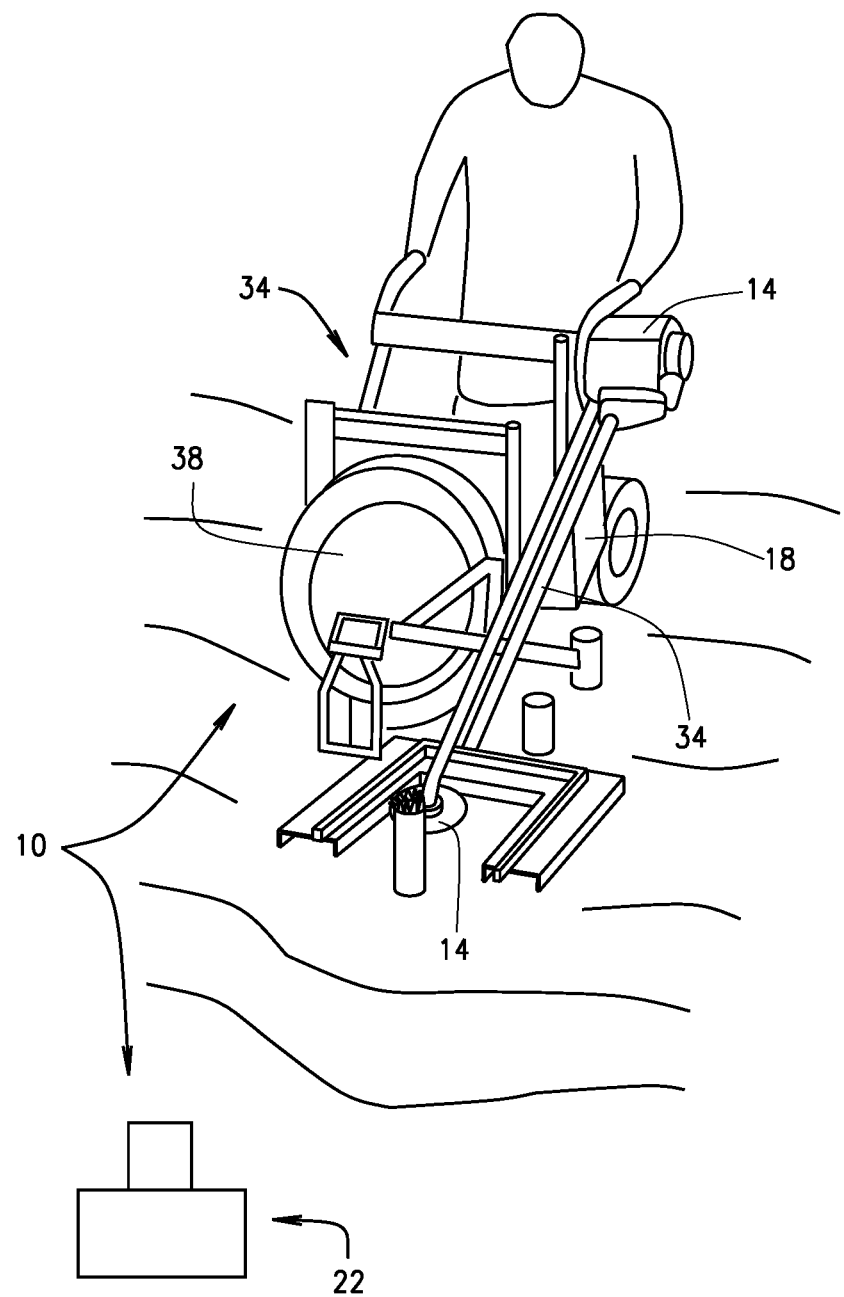
FIG. 5 is an exemplary front illustration of the post-harvest stalk strength determination system shown in FIG. 3 being used in a field, in accordance with various embodiments of the present disclosure.

Referring to FIGS. 3, 4 and 5, in various instances of the mobile platform mounted system 10, the system 10 can further comprise a stalk stump cutter guide 42 mounted to the mobile platform 34 and structured and operable to guide each stalk stump 26 into the blade(s) of the stalk stump cutter 14 and/or guide the blade(s) of the stalk stump cutter 14 into each stalk stump 26 such that each stalk stump 26 is prepared in a consistent manner at substantially the same height and at substantially the same angle, thereby enhancing the consistency of the acquired image data and the accuracy of the analysis thereof, and the resulting pre-harvest stalk strength determinations.

As exemplarily illustrated in FIGS. 3, 4 and 5, in various embodiments the mobile platform 34 can be motorized/self-propelled walk-behind mobile platform that comprises an engine or motor 46 that is operable and controllable to drive at least one wheel 50. In such instances, the mobile platform 34 comprises a chassis 54 to which the motor/engine 46 is fixedly mounted and the wheels 50 are rotationally mounted. As exemplarily illustrated, the system 10 includes the debris dispersion device that comprises a blower that is mounted to the chassis 54 and driven by the motor/engine 46. In the illustrated exemplary embodiments the stalk stump cutter 14 and the imaging device 18 are mounted to the chassis 54 via a support arm and bracket 58. As illustrated, the stalk stump cutter 14 is disposed forward of the imaging device 18, and the debris dispersion device 38 is disposed between the stalk stump cutter 14 and the imaging device 18. Therefore, as the mobile platform 34/system 10 travels down a row of post-harvest stalk stumps 26 the stalk stumps 26 are prepared, then the debris is dispersed/removed, then the image data is collected, as described above. Additionally, in the illustrated exemplary embodiments, the system 10 includes the stalk stump cutter guide 42 that is mounted to support arm and bracket 58.

Figure 7:
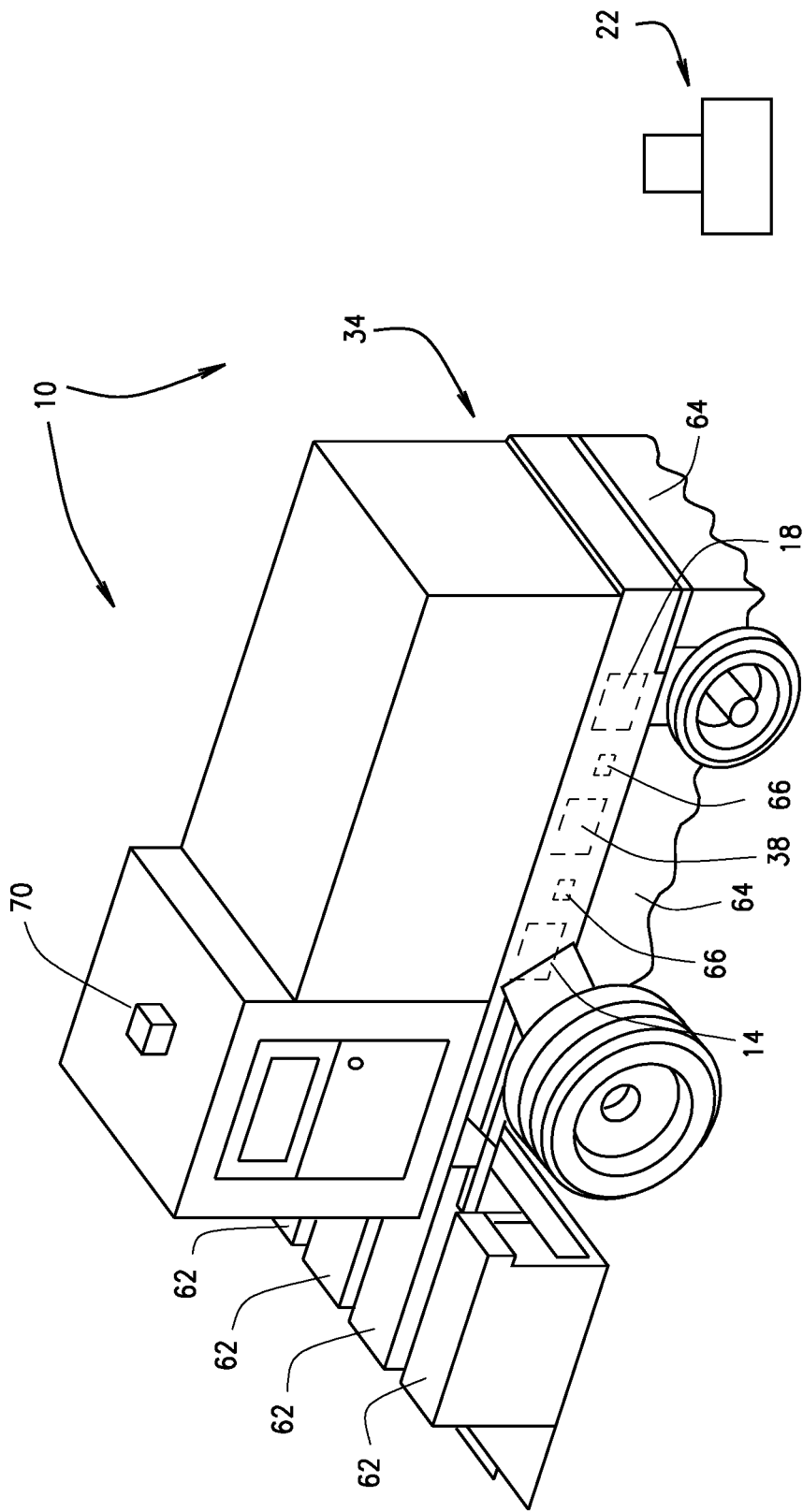
FIG. 7 is an exemplary isometric illustration of the post-harvest stalk strength determination system shown in FIG. 1 having the various components thereof mounted to a corn harvester mobile platform, in accordance with various embodiments of the present disclosure.

Referring now to FIG. 7, it is envisioned that in various embodiments, the mobile platform 34 can be a motorized/self-propelled riding vehicle such as a tractor or a corn harvester. For example, as exemplarily illustrated in FIG. 7, in various embodiments the mobile platform 34 can be a corn harvester that is structured and operable to harvest corn from corn plants in a field leaving behind the discarded post-harvest (e.g., unprepared, or pre-preparation) stalk stumps 26. In such embodiments, the stalk stump cutter 14 and the imaging device 18, and, in various instances, the debris dispersion device 38 can be mounted under the harvester. Accordingly, as the harvester is driven through a field of corn, the harvester will harvest the corn as is known in the art, leaving the discarded post-harvest/pre-preparation stalk stumps 26, Thereafter, as the harvester continues to travel though the field, the stalk stump cutter 14 will prepare the stalk stumps 26 to provide the substantially flat and even cross-sectional surfaces 30, the debris dispersion device 38 (if included) will disperse or remove the debris from around the base of freshly harvested and prepared stalk stumps 26, and the imaging device 18 will acquire the image data of the cross-sections 30 and communicate the image data to the data processing system 22. Thereafter, the image data is analyzed as described above. Hence, in such embodiments, the corn can be harvested and the stalk stumps 26 analyzed concurrently.

In such embodiments, the harvester typically will simultaneously harvest a plurality of rows of corn as the harvester traverses the field. Therefore, in such embodiments, and other envisioned embodiments, the system 10 can comprise a plurality of data collection subsystems, wherein each subsystem comprises a respective stalk stump cutter 14 and a respective imaging device 18, and in various instances a respective debris dispersion device 38. Specifically, the system 10 would comprise a number of data collection subsystems equal to the number of harvesting heads 62 the harvester includes. Each subsystem would have the respective components (e.g., the stalk stump cutter 14, the debris dispersion device 38 and the imaging device 18) linearly aligned with a respective one of the harvesting heads 62 such that as the harvester traverses the field harvesting the corn, thereby generating a plurality of rows of post-harvest/pre-preparation stalk stumps 26, each respective row of stalk stumps 26 can be prepared and the image data collected by the respective data collection subsystem concurrently with the harvesting.

As described above, in various embodiments, the corn harvester head(s) 62 can comprise the stalk stump cutter(s) 14.

In various embodiments wherein the mobile platform 34 is a motorized/self-propelled riding vehicle, in order to enhance the accuracy and consistency of the image data collected, the system 10 can further include a skirt or shroud 64 disposed around the bottom of the respective vehicle and suspended downward toward the ground (e.g., disposed around the bottom of a harvester and suspended toward the ground). The skirt/shroud 64 is disposed around a bottom of the corn harvesting machine to substantially enclose and shield an area beneath the mobile platform (e.g., the corn harvester) in which the imagining device(s) 18 is/are mounted from ambient light. More specifically, in various instances, the skirt/shroud 64 will be such that it will hang from the bottom of the mobile platform 34 such that the bottom of the skirt/shroud 64 will touch or nearly touch the ground. The skirt/shroud 64 is structured and operable to block a significant portion (e.g., 100% to 75%) of the ambient light from radiating or shining beneath the mobile platform 34. In such instances, the system 10 can further include one or more lights 66 or other light source (e.g., infrared (IR) lighting source(s)) disposed under the mobile platform 34 that are structured and operable to provide light or other illumination on at least the area around each prepared stalk stump 26 as the imaging device(s) 18 is/are collecting the image data. Particularly, the lighting source(s) 66 will provided a consistent light or other illumination (e.g., IR illumination) intensity for all image data collected, thereby improve the analysis and consistency of the image data collected and the resulting pre-harvest stalk strength determinations. Moreover, the skirt/shroud 64 shields the imaging device(s) field of view from chaff, plant debris, ambient light and/or other "noise" that may affect data collection and/or analysis. A controlled sensing environment like this would permit reliable and repeatable imaging/data collection to occur at substantially at any hour of the day and/or in any lighting conditions.

With further reference to FIG. 7, in various embodiments, the system 10 can comprise a global positioning system (GPS) 70 that is structured and operable to acquire location data of each stalk stump 26 as each stalk stump 26 is prepared, imaged and analyzed, and communicate such location data to the data processing system 22. Accordingly, comprehensive analysis of an entire field can provide corresponding location data with the respective stalk strength data for each stalk stump 26 in the field, which can be overlay with a field map that details various phenotype and genotype characteristics of each pre-harvest corn plant in the field. Although the GPS 70 is exemplarily shown in FIG. 7 in correlation with the harvester embodiments described above, it should be understood that the GPS 70 can be also included in the wall-behind embodiments described above.

Furthermore, it is envisioned that in various embodiments, the post-harvest stalk strength determination system 10 described above can be fully-automated, capable of using electronic geo-location (e.g., GPS data) to perform all of the activities necessary to assess the stalk strength of thousands or more plants per hour, thereby providing plant breeders with accurate and high-throughput system(s) and method(s) of estimating the pre-harvest stalk strength of thousands or more plants per hour. For example, the stalk strength analysis described above can be performed post-harvest to determine the stalk strength of the respective corn plants during the pre-harvest grain fill period, for a plurality of corn plants without damaging the plants. The stalk strength data obtained by the system(s) and method(s) described herein can be combined with other types of data collected about the plants' performance (e.g. yield, disease resistance) to provide plant breeders a highly-accurate, high-throughput method of assessing overall crop performance.

Referring now to FIGS. 8A and 8B, as described above, in various embodiments, wherein the mobile platform 34 can be a motorized/self-propelled riding vehicle such as a tractor or a corn harvester, the corn harvester head(s) 62 can comprise the stalk stump cutter(s) 14. In various instances of such embodiments, the imagine device(s) 18 and/or other desired imaging sensors can be disposed in a pull-behind imaging subsystem 74 that connected to the back end of the harvester 34 and pulled behind the harvester as the harvester 34 traverses the field. In such instances, as the harvester 34 traverses the field, it pulls the imaging subsystem 74 relative to the stalk stumps 26 so that the imaging devices 18 can collect images and/or other data related to the stalk pith of each stalk stump 26 as each stalk stump 26 passes through a field of view 78 of respective imaging device(s) 18. In various embodiments, the imaging subsystem 74 can include enclosure structure 82 having inner surfaces to which the imaging device(s) 18 is/are mounted. In various instances, the enclosure structure 82 can be opaque such that ambient light cannot pass therethrough.

In various embodiments, in order to enhance the accuracy and consistency of the image data collected, the imaging subsystem 74 can include a skirt or shroud 86 disposed around the bottom of the enclosure structure 82 and suspended downward toward the ground. The skirt/shroud 82 is disposed around a bottom of the enclosure structure 82 to substantially enclose and shield an area beneath the enclosure structure 82 in which the imagining device(s) 18 is/are mounted from ambient light. More specifically, in various instances, the skirt/shroud 86 will be disposed such that it will hang from the bottom of the enclosure structure 82 so that the bottom of the skirt/shroud 86 will touch or nearly touch the ground. The skirt/shroud 86 is structured and operable to block a significant portion (e.g., 75% to 100%) of the ambient light from radiating or shining beneath the enclosure 82 of the imaging subsystem 74. In such instances, the imaging subsystem 74 can comprise one or more lighting or illumination source 90 (e.g., an infrared (IR) illumination source) mounted to the enclosure inner surface that are structured and operable to provide light or other illumination (e.g., IR illumination) within the interior of the enclosure 82. Particularly, the lighting source(s) 90 will provided a consistent light or other illumination (e.g., IR illumination) intensity for all image data collected, thereby improve the analysis and consistency of the image data collected and the resulting pre-harvest stalk strength determinations. Moreover, the skirt/shroud 78 shields the imaging device(s) field of view 78 from chaff, plant debris, ambient light and/or other "noise" that may affect data collection and/or analysis. A controlled sensing environment like this will permit reliable and repeatable imaging/data collection to occur at substantially at any hour of the day and/or in any lighting conditions.

Although the stalk stump cutter(s) 14, the debris dispersion device(s) 38 and the imaging device(s) 18 have been described above with regard to various exemplary embodiments and locations thereof, it should be understood that; 1) the stalk stump cutting/preparation can be done using any suitable stalk stump cutter 14 that can be hand carried and operated, or located anywhere on any suitable mobile platform 34 or subsystem; 2) the debris from around each cut stalk stump 26 can be dispersed or removed using any debris dispersion device 38 that can be hand carried and operated, or located anywhere on any suitable mobile platform 34 or subsystem such that the debris is dispersed after the stalk stumps 26 are prepared by the respective stalk stump cutter 14 and prior to image collection by the respective imaging device(s) 18; and 3) the imaging and data collection of the prepared stalk stump cross-sections 30 of stalk stumps 26 can be collected at any time after the stalk stumps 26 have been cut using any imagine device(s) 18 that can be hand carried and operated, or located anywhere on any suitable mobile platform 34 or subsystem such that the image data can be collected at any time after the stalk stumps 26 are prepared by the respective stalk stump cutter 14.

Referring now to FIGS. 1 through 8B, it is envisioned that imaging device(s) 18, as described in any of the embodiments described herein, can comprise substantially any type of imaging device, sensor, (hyperspectral) camera, etc., that is useful for collecting image data or other energy values (e.g. digital images, IR images, intensities of electromagnetic energy at certain wavelengths, etc.) could be deployed within the system 10 to collect the data, depending on the user's objective. In various embodiments, the image data could be geospatially tagged as the post-harvest stalk strength determination system 10 is moved through the field, providing researchers with precise locations of each stalk stump 26 in a field and its respective stalk health score, based on analyzing the stalk pith using methods described herein.

Although the various embodiments of the mobile platform 34 have been exemplarily described herein as ground-contact vehicles, other forms of the mobile platform 34 are envisioned, such as (unmanned) aerial vehicles. Moreover, any means of moving the post-harvest stalk strength determination system 10 relative to the stalk stumps 26 could be used in conjunction with the methods disclosed herein.

Referring now to FIG. 9, FIG. 9 exemplarily illustrates several examples of how the post-harvest stalk strength determination system 10, such as that exemplarily illustrated in and described with regard to in FIGS. 8A and 8B can be used, in various instances, to harvest corn and/or collect stalk health data/images in a research field related to stalk health. In the part 1 of FIG. 9, stover and other lose plant debris is deposited alongside the mobile platform/combine 34 adjacent or in rows 1 and 4 (Plot A Row 1 and Plot B Row 4), while imaging can be conducted on header rows 2 and 3 (Plot A Row 2 and Blot B Row 3). Other combinations and/or permutations are envisioned. Part 2 of FIG. 9 exemplarily illustrates how a field of plants divided into separated (research) plots can be prepared and analyzed for stalk health during harvest. When the mobile platform/combine 34 turns at the end of the field and begins to work its way back, stover and/or plant debris from the current path of the harvester can be deposited such that it overlaps the stover/plant debris that was deposited from a previous path of the harvester.

Part 3 of FIG. 9 exemplarily illustrates how 4-row research plots can be prepared and analyzed for stalk health analysis contemporaneously with harvest. Other combinations and permutations of these examples are envisioned.

It should be understood that although the removal or dispersion of debris from around each cut stalk stump 26 has been described above utilizing the debris dispersion devices 38 exemplarily described above, it is envisioned that, in various embodiments, the post-harvest stalk strength determination system 10 can include any device, system, subsystem, mechanism or apparatus suitably structured and operable to remove or disperse from area surrounding the prepared stalk stump cross-sections 30 of stalk stumps 26 prior to the respective stalk stump cross-sections 30 being imaged via the imaging device(s) 18. For example, in various instances wherein the mobile platform 34 is a combine, the discharge (e.g., the severed portions of the stalks) can be funneled back into the combine and then deposited at a later time (e.g., out the rear of the combine) after the respective imaging data has been collected. Or, in other instances, the discharge can be deposited or funneled to a separate vehicle (e.g. truck, etc.) and used as stover.

EXPERIMENTAL EXAMPLES

The following are experimental examples of use of the post-harvest stalk strength determination system 10 as described above.

Experimental Example 1. Referring to FIGS. 10 and 11, in 2016, carbohydrate stress resulting from reduced levels of photosynthesis was induced in two sets of complementary trials. Sixty corn hybrids, i.e., 20 hybrids each from 100, 105 and 110 relative maturity (RM) groups, were planted in both sets of trials. Fifty-eight hybrids were common among the two sets of trials.

In one set of trials, leaves from the bottom half of plants (i.e., all leaves below the primary ear node) were physically removed between the R1 and R2 growth stages by stripping leaves from plants. Hybrids were replicated twice in a split-plot randomized complete block design with two replicates. The three RM groups were assigned to main plots and 20 hybrids per RM group were planted in two-row plots with about 40 plants per plot per hybrid in each sub-plot. Hence, mean incidence (%) of plants failing the push test and incidence (%) of plants with healthy stalks were calculated from a sample of about 80 plants per hybrid. These trials were repeated at two locations, Waterman, Illinois and Evansville, Indiana.

In the second set of trials, different levels of nitrogen fertilizer (N) and different plant population densities (D) were used to create different levels of photosynthetic and carbohydrate stresses. The four N×D treatments ranked from hypothesized least stress to most stress, included:

36K plants per acre with 240 lb N applied
42K plants per acre with 240 lb N applied
47K plants per acre with 180 lb N applied
42K plants per acre with 60 lb N applied Treatments were replicated twice in a split-split plot of a randomized complete block design. N+D treatments were applied to main plots; RM groups were assigned to sub-plots; and four-row plots of hybrids were planted in sub-sub-plots with approximately 40 plants per row. Incidence (%) of plants with healthy stalks were sampled from a single, middle row of four-row plots. Hybrid mean incidence (%) of plants with healthy stalks were calculated from a sample of approximately 320 plants per hybrid (40 plants per plot×2 replicates×4 N+D treatments). These trials were repeated at four locations, Mineral, Illinois, and Alburnett, Independence, and Green Mountain, Iowa.

Stalk strength of plants was tested with the "push test", a standard practice employed by corn growers for nearly 80 years to determine if a plant is likely to lodge. Within one to two weeks of harvest, individual plants are pushed at about waist height to 45 degrees of upright and released. Plants that return to close to an upright position "pass" the push test and are considered to have adequate stalk strength to prevent lodging prior to harvest. Plants with stalks that break or those that do not return to a nearly upright position "fail" the push test and are considered to be likely to lodge if strong winds or storms occur in the field prior to harvest.

In all trials, incidence of plants with healthy stalks was assessed by the method described herein using the post-harvest stalk strength determination system 10 described herein. Particularly, following harvest of corn grain, using the stalk stump cutter 14 (as described above), a clean cut was made across the corn stumps 26 that remained standing after combining, thus producing a cross section of the stalk stumps 26 at about the second internode above the soil line. Pith tissues were examined from each the cross section and placed into one of two categories: healthy—50% or more of the pith tissue intact; or unhealthy—less than 50% of the pith tissue intact. Stalks stumps with less than 50% of pith tissue intact frequently were discolored and rotted as the result of fungal colonization. Incidence (%) of plants passing the push test and incidence (%) of plants with healthy stalks were measured (using the system 10 described herein) from the same plots (plants) in the trials at Waterman, Illinois and Evansville, Indiana. The association between the push test and the stalks determined to be healthy using the system 10 was examined from scatterplots and correlations of the means of the 60 hybrids in each trial (FIG. 10). Similarly, the association between incidence of plants passing the push test in the Waterman and Evansville trials and incidence of plants with determined (via system 10) to have healthy stalks in the four N+D trials was examined from scatterplots and correlations of means of the 58 hybrids common to the two sets of trials (FIG. 11).

Experimental Example 2. Referring now to FIG. 12, during the corn growing season of 2017, another set of experiments were conducted to test the efficacy of determining stalk strength by examining post-harvest discard utilizing the post-harvest stalk strength determination system 10 described herein. The experiments were similar to the 2016 carbohydrate stress trials described herein. Experiments comprised 4 repetitions of plots planted with a 110 RM hybrid at four different locations in the USA (Huxley, Iowa; Jerseyville, Illinois; Waterman, Illinois; Fort Branch, Indiana). At each location, two of the repetitions served as the experimental group and were subjected to carbohydrate stress by leaf stripping, as described in Example 1, the other two repetitions served as controls (not stripped). Each repetition comprised 72 plants planted in two 11 ft rows, 18 plants/row.

At harvest time, all plants were subjected to the push test as described in Example 1, and the color of each stalk noted as either green or brown. Following combine harvest, the usually-discarded stalk stumps were prepared using system 10 as described above, and analyzed as described in Example 1. The mean incidence (%) of plants failing the push test and incidence (%) of plants with healthy stalks were calculated for each repetition. FIG. 12 reveals the association between the push test and healthy stalks for the Waterman trials; the results from analyzing the data and results generated from the other sites were similar. Note that the slope in this figure is positive because the Y-axis=% passed, instead of % failed (which is the opposite of FIG. 10).

Experimental Example 3. In 2018, two sets of tests were conducted; a first set in which stalk stress was induced by N restriction and increased D in a first set of corn plants of the 100, 105, and 110 RMs (relative maturity groups), and a second set in which stalk stress was induced only by increased D on a second set of corn plants from the 95, 115, and 120 RMs. The stalk stress was induced to create populations with diverse stalk health to test the methods disclosed herein and demonstrate that they can be used with a diverse range of accompanying technologies, including automated vehicles and computer algorithms.

In the N+D trials, a first group was planted at higher planting density (44 k plants/acre) and a second group was planted at a lower planting density (38 k plants/acre). The higher-density population received a 60 lbs/acre treatment of N just prior to planting, and then a side dress of additional 60 lbs/acre of N later as a side dress. The lower-density population was provided with only the pre-plant N 60 lbs/acre treatment. Four replications per RM were conducted, with two replicates per N treatment, resulting in about 84-96 hybrids tested, depending on the RM. These replications were repeated at five United States locations (Tripoli, Iowa; De Soto, Iowa; Shabbona, Illinois; Oskaloosa, Iowa; and Raritan, Illinois).

In the D only trials, plants were grown at one of two densities (42 k plants/acre or 48 k plants/acre) at three different US locations; four replications per planting location per density for a total of 8 reps for each of the three RMs at each location.

In each set of trials, following combine harvest, the stalk stumps discarded were prepared using system 10 as described above, and scored manually as either healthy or unhealthy, as described in Example 1. Then, a camera onboard an unmanned aerial vehicle (UAV) was flown over the plots to collect overhead images of the stalk stumps and the exposed pith region of the plants. The images were then analyzed by an algorithm designed to distinguish stalks and score the integrity of the pith tissue, analogously to how manual scoring is performed by a human on foot.

Results were encouraging, as both methods were able to reliably differentiate most stalks and assign them into health vs. unhealthy categories. Figure A5 shows examples of images collected by the UAV and scored by the algorithm, including examples of RGB thresholds the algorithm used to make its calls.

Experimental Example 4. Tests were conducted of the system 10 and automated methods of preparing post-harvest discard (corn stalk stumps) for stalk health analysis, as described herein. Reliable cross-sections with sufficiently clean and uniform surfaces that the automated image analysis and/or manual scoring methods described herein could be used to score stalk pith health was achieved by using a commercially-available combine modifies with one or more stalk stump cutter(s) 14 (as described above), and/or an auto-head height control, and/or a row guidance system, and/or a cornrower device to help move debris and stover away from the stalk stumps. This system was successfully used to prepare stalk stumps for scoring during the 2018 Trials described in Example 3.

As used herein, stalk health refers broadly to the health of the cells and/or tissues comprising the plant stalk and are not limited to scoring plants for specific types of diseases or stalk performance. For example, the methods disclosed herein could be used to score plants for tolerance and/or resistance to infection by substantially any pathogen, especially those known to infect plant stalks, or affect the heath of the stalk and/or its performance, be they fungal, bacterial, viruses or any other type of infection. These methods could also be used to rate plants for other causes or symptoms of weakened stalk, for example, greensnap and/or other genetically-related stalk health issues. Stalk health also includes consequences to, or responses by, the plant to exposure to chemicals and/or exposure to anything moving through the growing area and/or interacting with the plants (e.g. any type of person, animal, machine, etc., known to be useful for the cultivation of plants). Nonlimiting examples include assessing the damage parts of a machine cause the plants as they traverse through, or over, the field and/or interact with the plants to sense information, apply treatments, collect samples, etc. For example, the efficacy and consequences of using mechanized, non-disruptive plant touch, or plant contact, sensing systems, like those described in: 1) U.S. patent application Ser. No. 15/502,548, filed Feb. 8, 2017, and titled Apparatus And Methods For In-Field Data Collection And Sampling: and/or 2) U.S. patent application Ser. No. 16/089,796, filed Sep. 28, 2018, and titled Stem Sensor; and/or 3) U.S. patent application Ser. No. 14/353,036, filed Apr. 21, 2014, and titled Plant Stand Counter; and/or 4) U.S. patent application Ser. No. 15/350,169, filed Nov. 14, 2016, and titled Plant Stand Counter, could be assessed.

The Applicant/assignee of the above referenced Ser. Nos. 15/502,548, 16/089,796, 14/353,036 and 15/350,169 patent applications is the same Applicant/assignee of the present application, and the above referenced Ser. Nos. 15/502,548, 16/089,796, 14/353,036 and 15/350,169 patent applications are incorporated by reference herein in their entirety such that it is envisioned that in various embodiments one or more or all the components described in one or more of the above referenced Ser. Nos. 15/502,548, 16/089,796, 14/353,036 and 15/350,169 patent applications can be combined with and/or included in the post-harvest stalk strength determination system 10 described above, and/or vice-versa.

The description herein is merely exemplary in nature and, thus, variations that do not depart from the gist of that which is described are intended to be within the scope of the teachings. Moreover, although the foregoing descriptions and the associated drawings describe example embodiments in the context of certain example combinations of elements and/or functions, it should be appreciated that different combinations of elements and/or functions can be provided by alternative embodiments without departing from the scope of the disclosure. Such variations and alternative combinations of elements and/or functions are not to be regarded as a departure from the spirit and scope of the teachings.

What is claimed is:

1. A system for post-harvest or at-harvest determination of pre-harvest strength of a corn stalk, said system comprising:
    a stalk stump cutter structured and operable to cut a post-harvest stalk stump to provide a substantially flat and even cross-sectional surface of the stalk stump;
    an imaging device structured and operable to acquire image data of the stalk stump cross-section; and
    a computer based data processing system structured and operable to analyze the image data and determine a pre-harvest stalk strength of the corresponding stalk.

2. The system of claim 1 further comprising a mobile platform to which stalk stump cutter is mounted, the mobile platform structured and operable to traverse a field in which a plurality of stalk stumps exist such that stalk stump cutter can cut a plurality of post-harvest stalk stumps in the field at substantially the same height as the mobile platform traverses the field.

3. The system of claim 1 further comprising a mobile platform to which stalk stump cutter is mounted, the mobile platform structured and operable to traverse a field in which a plurality of stalk stumps exist such that stalk stump cutter can cut a plurality of post-harvest stalk stumps in the field at substantially the same height as the mobile platform traverses the field, wherein the imaging device is mounted to the mobile platform such that image data can be acquired of each of the stalk stump cross-sections as the mobile platform traverses the field.

4. The system of claim 3 further comprising a GPS device mounted to the mobile platform to acquire location data of each stalk stump.

5. The system of claim 3, wherein the mobile platform comprises a corn harvesting machine structured and operable to:
    harvest the corn plants in the field such that the stalk stumps are generated;
    cut the stalk stumps to provide the substantially flat and even cross-sections; and
    acquire the image data of each stalk stump cross-section.

6. The system of claim 5 further comprising a skirt disposed around a bottom of the corn harvesting machine, the skirt structured and operable to substantially enclose and shield from ambient light an area beneath the corn harvesting machine in which the imagining device is mounted.

7. The system of claim 3 further comprising a debris removal device structured and operable to remove debris from an area around the stalk stump prior to acquiring the imaging data.

8. A method for determining a pre-harvest stalk strength of a corn plant after or at the same time as the corn plant is harvested, said method comprising;
    cutting a post-harvest stalk stump, utilizing a stalk stump cutter of a stalk strength determination system, to provide a substantially flat and even cross-sectional surface of the stalk stump;
    acquiring image data of the stalk stump cross-section; and
    analyzing the image data and determining a pre-harvest stalk strength of the corresponding stalk.

9. The method of claim 8, wherein:
    the image data of the stalk stump cross-sectional surface is acquired utilizing an imaging device of the stalk strength determination system; and
    the image data is analyzed and the pre-harvest stalk strength of the corresponding stalk is determined utilizing a computer based data processing system of the stalk strength determination system.

10. The method of claim 8, wherein cutting the post-harvest stalk stump comprises cutting the stalk stump between the 2nd and 3rd internodes of the stalk stump.

11. The method of claim 9, wherein analyzing the image data comprises assaying the image data to determine the amount of damaged or missing tissue in a pith region of the stalk stump cross-section.

12. The method of claim 11, wherein analyzing the image data further comprises assigning a post-harvest score to the stalk stump based on the assay, wherein the score corresponds to pre-harvest stalk strength of the respective corn plant.

13. The method of claim 12, wherein assigning a post-harvest score to the stalk stump based on the assay, comprises assigning a post-harvest score to the stalk stump based on the assay, wherein the score corresponds to pre-harvest stalk strength at the R6 growth stage of the respective corn plant.

14. The method of claim 9 further comprising traversing a field in which a plurality of stalk stumps exist with a mobile platform having the stalk stump cutter mounted thereto, and cutting a plurality of the plurality of stalk stumps in the field at substantially the same height, via the stalk stump cutter, as the mobile platform traverses the field.

15. The method of claim 14, wherein the imaging device is mounted to the mobile platform, and the method further comprises acquiring image data of each of the stalk stump cross-sections as the mobile platform traverses the field.

16. The method of claim 15, wherein the mobile platform comprises a corn harvesting machine having the stalk stump cutter and the imaging device mounted thereto, and the method comprises:
    harvesting the corn plants in the field, via the corn harvesting machine, such that the stalk stumps are generated as the corn harvesting machine traverses the field;

cutting the stalk stumps to provide the substantially flat and even cross-sections as the corn harvesting machine traverses the field; and acquiring the image data of each stalk stump cross-section as the corn harvesting machine traverses the field.

17. The method of claim 16, wherein the stalk stump cutter and the imaging device are mounted under the corn harvesting machine, and acquiring the image data comprises disposing a skirt around a bottom of the corn harvesting machine to substantially enclose and shield an area beneath the corn harvesting machine in which the imagining device is mounted from ambient light.

18. The method of claim 9 further comprising acquiring location data of each stalk stump, via a GPS device mounted to the mobile platform as each stalk stump is cut.

19. The method of claim 9, wherein analyzing the image data comprises at least one of:

assaying the image data to determine a color of the tissue in a pith region of the stalk stump cross-section;

assaying the image data to determine the amount of damaged or missing tissue in a pith region of the stalk stump cross-section caused by a disease; and assaying the image data to determine the amount of damaged or missing tissue in a pith region of the stalk stump cross-section caused by interaction of the stalk strength determination system with the stalk.

* * * * *